(12) United States Patent
Raanes et al.

(10) Patent No.: US 7,623,623 B2
(45) Date of Patent: Nov. 24, 2009

(54) NON-COLLOCATED IMAGING AND TREATMENT IN IMAGE-GUIDED RADIATION TREATMENT SYSTEMS

(75) Inventors: Chris A. Raanes, Portola Valley, CA (US); Calvin R. Maurer, Jr., Mountain View, CA (US); Gopinath Kuduvalli, San Jose, CA (US); Michael J. Saracen, Oakland, CA (US)

(73) Assignee: Accuray Incorporated, Sunnyvale, CA (US)

( * ) Notice: Subject to any disclaimer, the term of this patent is extended or adjusted under 35 U.S.C. 154(b) by 54 days.

(21) Appl. No.: 11/824,125

(22) Filed: Jun. 29, 2007

(65) Prior Publication Data
US 2009/0003523 A1 Jan. 1, 2009

(51) Int. Cl.
*A61N 5/10* (2006.01)
*A61B 6/02* (2006.01)

(52) U.S. Cl. .................... 378/65; 378/68; 378/205; 600/427

(58) Field of Classification Search .............. 379/8, 379/20, 65, 68, 69, 95, 195, 205; 600/427
See application file for complete search history.

(56) References Cited

U.S. PATENT DOCUMENTS 5,117,829 A * 6/1992 Miller et al. ............... 600/427
5,207,223 A * 5/1993 Adler ......................... 600/427
5,724,400 A * 3/1998 Swerdloff et al. ............ 378/65
6,307,914 B1 10/2001 Kunieda et al.
6,385,288 B1 * 5/2002 Kanematsu .................. 378/65
6,422,748 B1 * 7/2002 Shepherd et al. ............ 378/203
6,516,046 B1 * 2/2003 Frohlich et al. .............. 378/65
6,535,574 B1 * 3/2003 Collins et al. ................ 378/65
6,842,502 B2 * 1/2005 Jaffray et al. ................ 378/65
6,865,254 B2 * 3/2005 Nafstadius ................... 378/65
6,914,959 B2 * 7/2005 Bailey et al. ................. 378/65
7,207,715 B2 * 4/2007 Yue ............................ 378/205
7,302,033 B2 * 11/2007 Carrano et al. .............. 378/41
2005/0201516 A1 * 9/2005 Ruchala et al. .............. 378/65
2007/0003021 A1 1/2007 Guertin et al.

OTHER PUBLICATIONS

E Coste-Maniere et al., "Robotic Whole Body Stereotactic Radiosurgery: Clinical Advantages of the CyberKnife® Integrated System", Paper Accepted: Dec. 1, 2004, Published online: Jan. 15, 2005. Copyright 2005 Robotic Publications Ltd., Available from: www.roboticpublications.com, Int J Medical Robotics and Computer Assisted Surgery 2005; 1(2); 28-39.

* cited by examiner

*Primary Examiner*—Edward J Glick
*Assistant Examiner*—Thomas R Artman
(74) *Attorney, Agent, or Firm*—Blakely, Sokoloff, Taylor & Zafman LLP

(57) ABSTRACT

An image-guided radiation treatment system includes a robotic positioning system and a tracking system that enables a radiation target to be imaged and aligned at one location and treated at another location by transferring positional data from the imaging system to the positioning system and the radiation treatment system.

52 Claims, 17 Drawing Sheets

NON-COLLOCATED IMAGING AND TREATMENT IN IMAGE-GUIDED RADIATION TREATMENT SYSTEMS

TECHNICAL FIELD

Embodiments of the present invention are related to the field of image-guided systems and, in particular, to image-guided radiation treatment systems.

BACKGROUND

Pathological anatomies such as tumors and lesions can be treated with an invasive procedure, such as surgery, which can be harmful and full of risks for the patient. A non-invasive method to treat a pathological anatomy (e.g., tumor, lesion, vascular malformation, nerve disorder, etc.) is external beam radiation therapy, which typically uses a linear accelerator (LINAC) to generate x-rays. In one type of external beam radiation therapy, an external radiation source directs a sequence of x-ray beams at a tumor site from multiple angles, with the patient positioned so the tumor is at the center of rotation (isocenter) of the beam. As the angle of the radiation source changes, every beam passes through the tumor site, but passes through a different area of healthy tissue on its way to and from the tumor. As a result, the cumulative radiation dose at the tumor is high and the average radiation dose to healthy tissue is low.

The term "radiosurgery" refers to a procedure in which radiation is applied to a target region at levels that are sufficient to necrotize a pathology. Radiosurgery is typically characterized by relatively high radiation doses per treatment (e.g., 1000-2000 centiGray), extended treatment times (e.g., 45-60 minutes per treatment) and hypo-fractionation (e.g., one to three days of treatment). The term "radiotherapy" refers to a procedure in which radiation is applied to a target region for therapeutic, rather than necrotic, purposes. Radiotherapy is typically characterized by a low dose per treatment (e.g., 100-200 centiGray), shorter treatment times (e.g., 10 to 30 minutes per treatment) and hyper-fractionation (e.g., 30 to 45 days of treatment). For convenience, the term "radiation treatment" is used herein to mean radiosurgery and/or radiotherapy unless otherwise noted.

Image-guided radiation treatment (IGRT) systems include gantry-based systems and robotic-based systems. In gantry-based systems, the radiation source is attached to a gantry that moves around a center of rotation (isocenter) in a single plane. The radiation source may be rigidly attached to the gantry or attached by a gimbaled mechanism. Each time a radiation beam is delivered during treatment, the axis of the beam passes through the isocenter. Treatment locations are therefore limited by the rotation range of the radiation source, the angular range of the gimbaled mechanism and the degrees of freedom of a patient positioning system. In robotic-based systems, such as the CyberKnife® Robotic Radiosurgery System manufactured by Accuray Incorporated of California, the radiation source is not constrained to a single plane of rotation and has five or more degrees of freedom.

In conventional image-guided radiation treatment systems, patient tracking during treatment is accomplished by comparing two-dimensional (2D) in-treatment x-ray images of the patient to 2D digitally reconstructed radiographs (DRRs) derived from three dimensional (3D) pre-treatment diagnostic imaging data of the patient. The pre-treatment imaging data may be computed tomography (CT) data, cone-beam CT, magnetic resonance imaging (MRI) data, positron emission tomography (PET) data or 3D rotational angiography (3DRA), for example. Typically, the in-treatment x-ray imaging system is stereoscopic, producing images of the patient from two or more different points of view (e.g., orthogonal projections).

A DRR is a synthetic x-ray image generated by casting (mathematically projecting) rays through the 3D imaging data, simulating the geometry of the in-treatment x-ray imaging system. The resulting DRR then has the same scale and point of view as the in-treatment x-ray imaging system, and can be compared with the in-treatment x-ray images to determine the position and orientation of the patient (and the radiation target within the patient). Different patient poses are simulated by performing 3D transformations (rotations and translations) on the 3D imaging data before each DRR is generated.

Each comparison of an in-treatment x-ray image with a DRR produces a similarity measure or equivalently, a difference measure, which can be used to search for a 3D transformation that produces a DRR with a higher similarity measure to the in-treatment x-ray image. When the similarity measure is sufficiently maximized (or equivalently, a difference measure is minimized), the corresponding 3D transformation can be used to align the patient in the radiation treatment system so that the actual treatment conforms to the treatment plan.

In conventional image-guided systems, the center of the imaging system (imaging center) and the center of the radiation treatment system (treatment center) are approximately collocated, which allows the imaging, patient alignment and treatment operations to be closely coupled during the treatment session.

However, co-location of the two systems may have disadvantages in some cases. In one case, one or more components of the imaging system (e.g., an imaging x-ray source or detector) may physically block the movement of the radiation treatment source to a desired/required treatment location. In another case, the radiation treatment source may block one of the x-ray imaging beam paths and interfere with stereoscopic imaging. In yet another case, patient positioning within the treatment delivery system may be restricted by the imaging system.

One type of gantry-based IGRT system, known as a portal imaging system, uses one or more LINACs at one or more positions to perform radiation treatment and imaging. FIG. 1 illustrates a conventional gantry-based IGRT system 100 with portal imaging. In FIG. 1, gantry 101 includes LINAC(s) 102 and a portal imaging detector 103 that rotate around an isocenter 104 where a patient on a treatment couch would be located for treatment. In one version, the system includes one LINAC that operates at a high energy level for radiation treatment and at a lower energy level for imaging. In another version, the system may include one high energy LINAC for radiation treatment and a second, lower energy LINAC for imaging. For radiation treatment, the radiation beam is collimated and/or shaped to concentrate radiation on a targeted pathology. For imaging, the beam is un-collimated to generate a wider field of view.

Portal imaging has some significant disadvantages. The images have low contrast because the high-energy radiation treatment beam is used for imaging and the differential absorption of different tissue types is low. The images also have more "noise" due to Compton scattering and secondary electron emissions associated with the high-energy beam. Another disadvantage is that because there is only one x-ray source and one x-ray detector for imaging, the gantry must be rotated between two positions in order to generate a pair of stereoscopic images. These disadvantages render portal imaging a poor candidate as the primary imaging system in an image-guided radiation treatment system.

BRIEF DESCRIPTION OF THE DRAWINGS

The present invention is illustrated by way of example, and not by way of limitation, in the figures of the accompanying drawings, in which.

DETAILED DESCRIPTION

Figure 1:
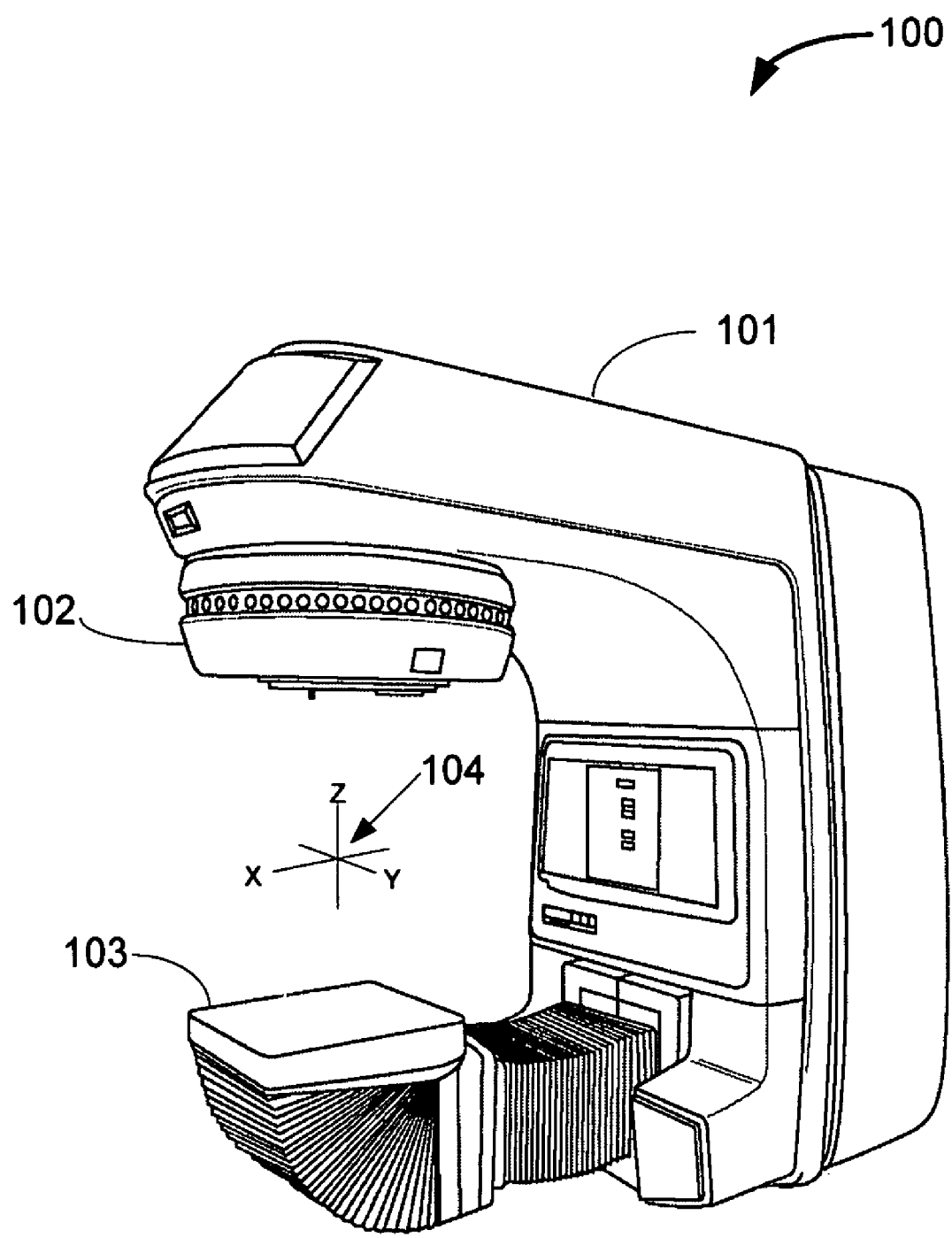
FIG. 1 illustrates a conventional gantry-based image-guided radiation treatment system with portal imaging.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. The term "x-ray image" as used herein may mean a visible x-ray image (e.g., displayed on a video screen) or a digital representation of an x-ray image (e.g., a file corresponding to the pixel output of an x-ray detector). The term "live x-ray image" or "intra-operative image" as used herein may refer to images captured at any point in time during an imaging or treatment delivery phase of a radiosurgery or radiotherapy procedure, which may include times when the radiation source is either on or off.

Unless stated otherwise as apparent from the following discussion, it will be appreciated that terms such as "generating," "registering," "determining," "aligning," "positioning," "processing," "computing," "selecting," "estimating," "comparing," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

Methods and apparatus for imaging and treating a radiation target at different locations are described that allow a radiation treatment system to operate without interference with an imaging system. In one embodiment, the apparatus employs a positioning system that acquires positional data on the radiation target at the imaging location and then transfers the radiation target and the positional data to a radiation system for treatment at a different location where movement of the radiation target can be detected, corrected by the positioning system and/or compensated for by the radiation system. In one embodiment, a tracking system may be used to track and detect movement of the radiation target in the radiation system. In another embodiment, a secondary imaging system at the treatment location may be used to detect movement of the radiation target in the radiation system. Other exemplary embodiments of the invention will become apparent from the following description in conjunction with the accompanying drawings.

Figure 2:
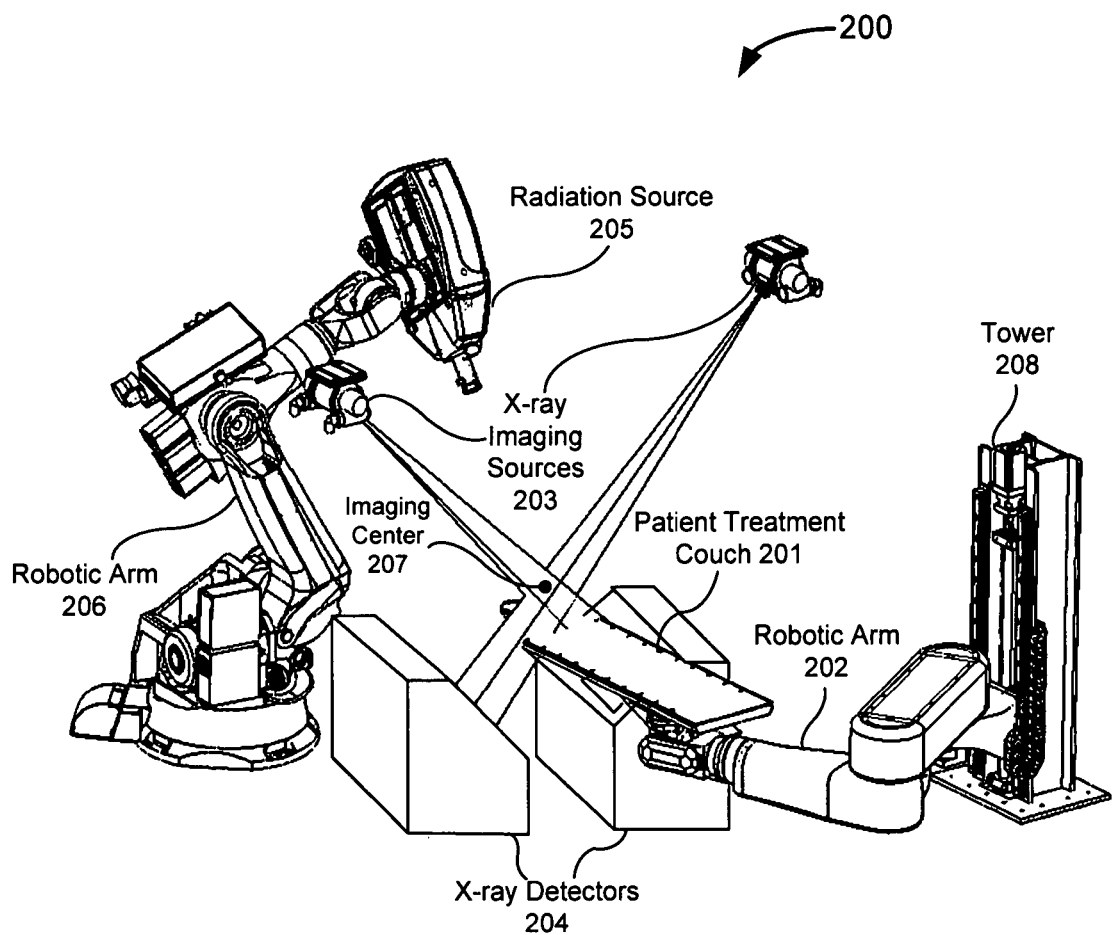
FIG. 2 illustrates a robotic image-guided radiation treatment system with collocated imaging and treatment systems.

FIG. 2 illustrates a robotic image-guided radiation treatment system 200, with collocated imaging and treatment centers such as certain configurations of the CyberKnife® Robotic Radiosurgery System manufactured by Accuray Incorporated of Delaware, for example. In this system, the imaging system and the radiation system are collocated so that the patient is in the field of view of the imaging system while treatment is applied to a pathological anatomy in the field of view. System 200 includes a radiation source 205 (e.g., a LINAC) controlled by a robotic control arm 206. System 200 also includes an imaging system that includes x-ray imaging sources 203 and x-ray detectors 204. System 200 also includes a patient positioning system, such as the RoboCouch® Treatment Couch System manufactured by Accuray Incorporated of Delaware, that includes a patient treatment couch 201, a robotic control arm 202 to position the patient in the field of view of the imaging system and a tower 208 to control the elevation of the robotic arm and couch. In system 200, the center of the imaging system (imaging center 207), defined as the intersection of the axes of the imaging beams from x-ray imaging sources 203, is approximately collocated with the center of treatment of system 200. This configuration may require programming of the robotic arm 206 to prevent the radiation source 205 from interfering with the imaging system components (i.e., sources 203 and detectors 204) in addition to avoiding contact with the patient treatment couch 201 and the patient positioned on the couch.

Figure 3:
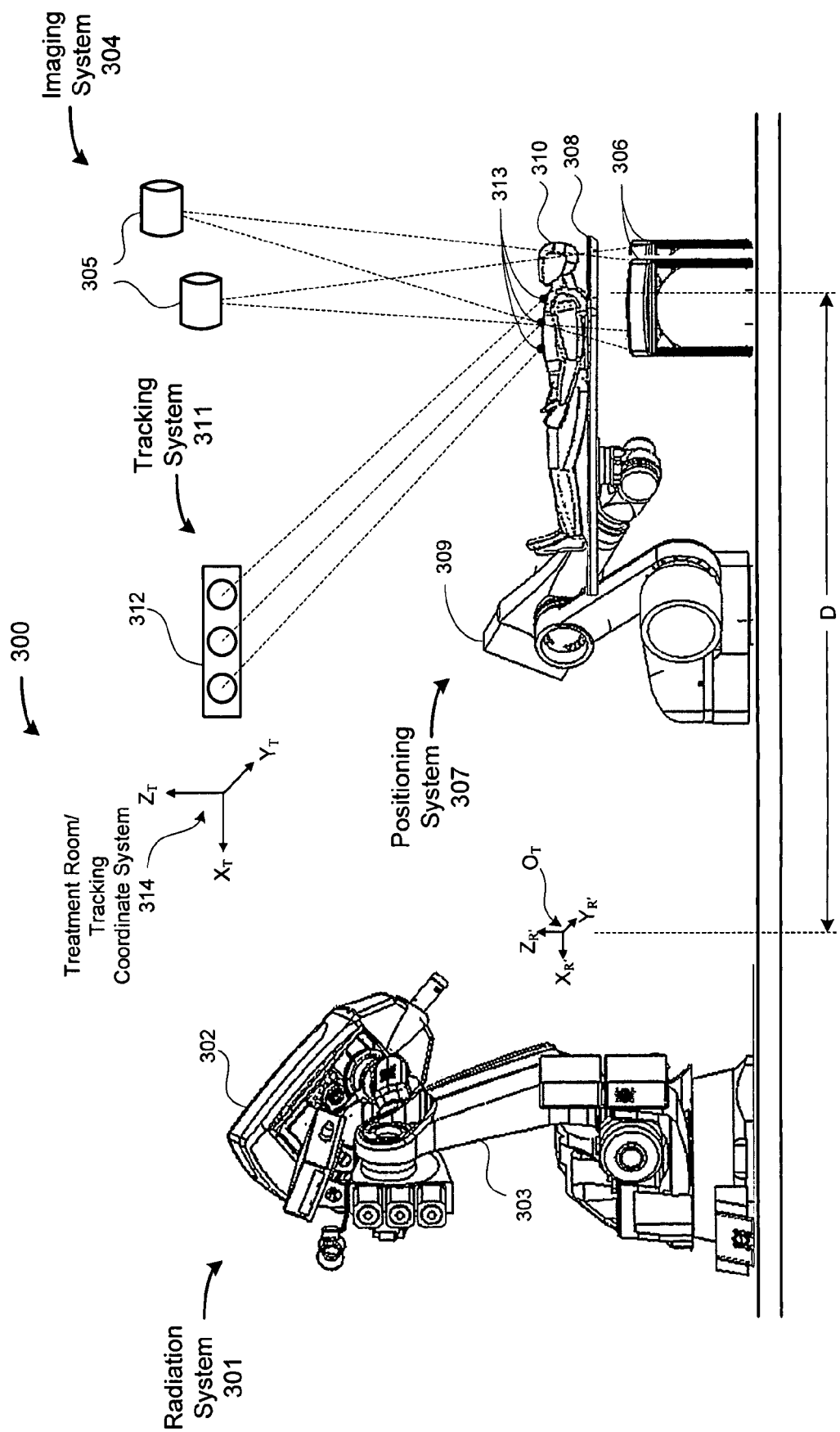
FIG. 3 illustrates an image-guided radiation treatment system in a first configuration in one embodiment.

One aspect of the present invention is an image-guided radiation treatment delivery system having non-collocated imaging and treatment centers. FIG. 3 illustrates an image-guided radiation treatment system 300 in one embodiment. System 300 includes an imaging system 304, a radiation system 301, a patient positioning system 307 and a tracking system 311. Radiation system 301 includes a radiation source 302 and a robotic control arm 303. Imaging system 304 includes x-ray imaging sources 305 and x-ray detectors 306. Patient positioning system 307 includes a treatment couch 308 and a robotic control arm 309 to position a patient 310 and which may be used to move the patient between the imaging system 304 and the radiation system 301 as described below. The robotic arm may have five or more degrees of freedom such that the couch 308 may be moved in three independent translations and three independent rotations. In one embodiment, patient positioning system 307 may be a RoboCouch™ Patient Positioning System manufactured by Accuray Incorporated of Delaware. In other embodiments, patient positioning system 307 may be any other positioning system as is known in the art (e.g., as illustrated in FIG. 2).

Figure 4:
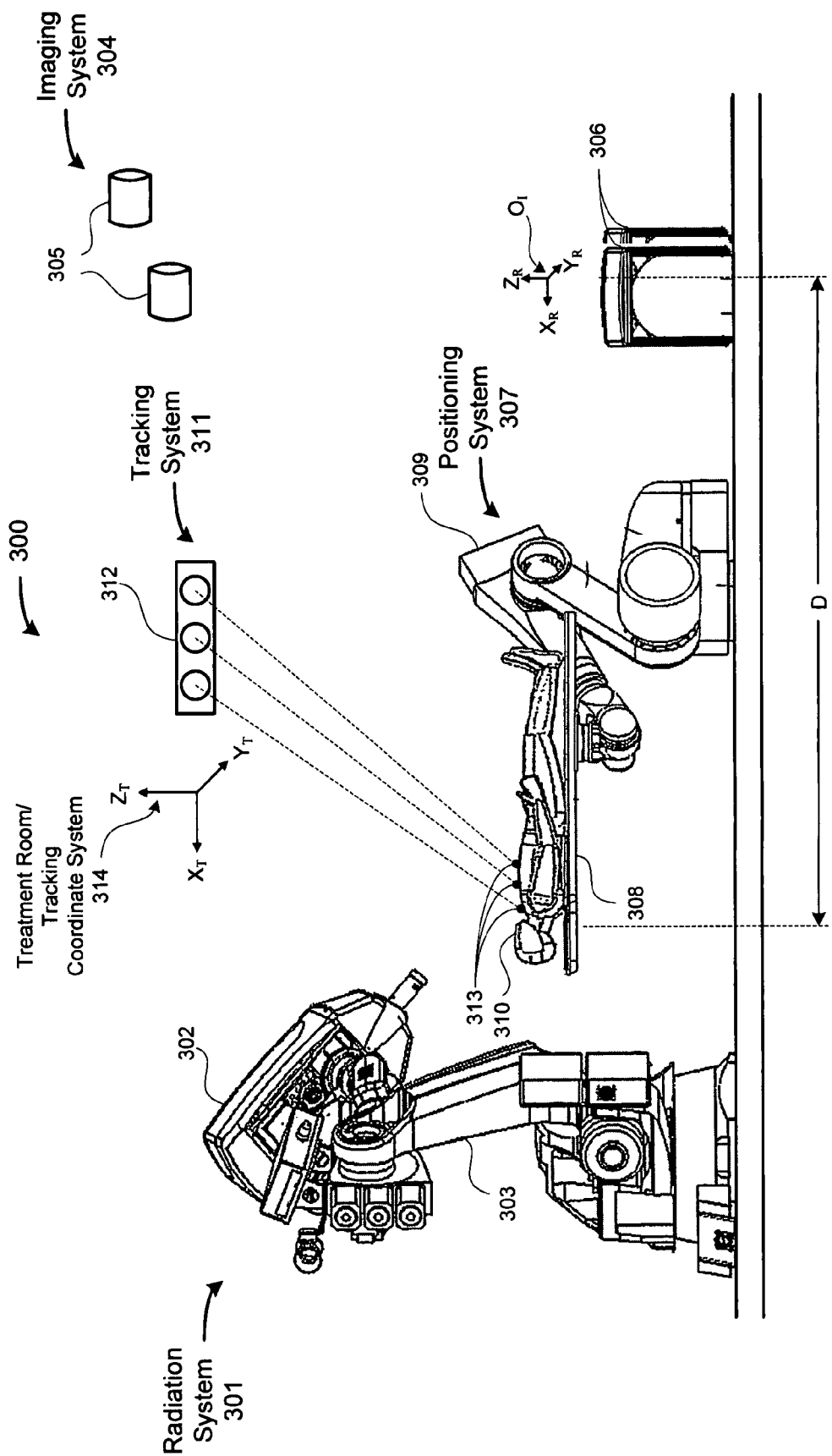
FIG. 4 illustrates the image-guided radiation treatment system of FIG. 3 in a second configuration in one embodiment.

Tracking system 311 may be calibrated to a treatment room coordinate system 314 and may be configured to track the location of the patient in the image-guided radiation treatment system 300, and may include a tracking apparatus (e.g. a tracking source and/or detector 312) and tracking devices 313 attached to patient 310. In the configuration of system 300 illustrated in FIG. 3, the patient 310 is positioned in the imaging system 304 so that a radiation target in a volume of interest (VOI) in the patient 310 can be aligned at an imaging center $O_I$ (illustrated in FIG. 4) of the imaging system 304. In one embodiment, as illustrated in FIGS. 3 and 4, a radiation treatment center $O_T$ in radiation system 301 may be separated from an imaging center $O_I$ in imaging system 304 by a distance D, such that the components of imaging system 304 are located beyond the range of motion of radiation source 302. In other embodiments, the distance D may be a lesser distance such that radiation system 301 and imaging system 304 are separated by a distance beyond the planned range of motion of radiation source 302 during treatment.

In one embodiment, the VOI containing a pathological anatomy (the "target") is identified and delineated during a pre-operative diagnostic and treatment planning phase, using 3D scan data such as computed tomography (CT), magnetic resonance imaging (MRI), positron emission tomography (PET), 3D rotational angiography (3DRA) or the like. The VOI is rendered as one or more DRRs in each of two or more projections corresponding to a range of patient orientations corresponding to a known geometry of the x-ray imaging system 304. In one embodiment, DRR generation may be performed during the pre-operative phase. In another embodiment, DRR generation may be performed inter-operatively in conjunction with live x-ray imaging.

In a first phase of the operative procedure in one embodiment, the imaging and registration phase, the patient 310 is placed on the treatment couch 308. The positioning system 307 may be used to move the patient such that the VOI is positioned in the field of view of the x-ray imaging system 304 in proximity to the center of the x-ray imaging system (imaging center $O_I$), which has known coordinates in the treatment room coordinate system 314. While the patient is positioned in the imaging system 304, 2D x-ray images of the VOI (including the defined radiation treatment target) may be captured by the imaging system 304. The 2D x-ray images may be registered with one or more 2D reference DRRs of the VOI in each projection of the x-ray imaging system 304, and search algorithms may be used to find a 3D transformation between the position of the patient in the imaging system (represented by the live x-ray images) and a reference position of the patient (represented by the DRRs) associated with the treatment plan.

Figure 14:
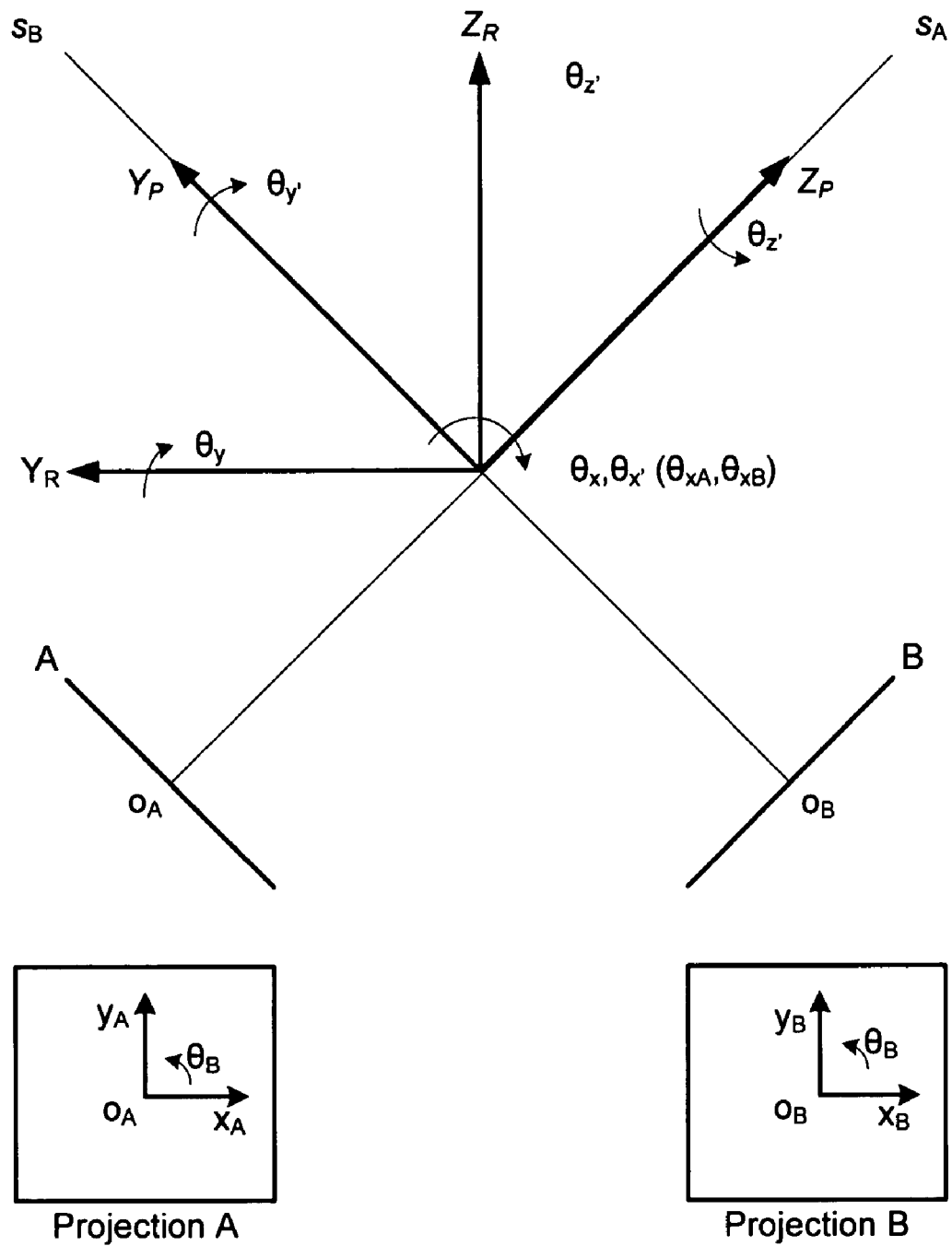
FIG. 14 illustrates a 3D coordinate system transformation in one embodiment.
Figure 15A:
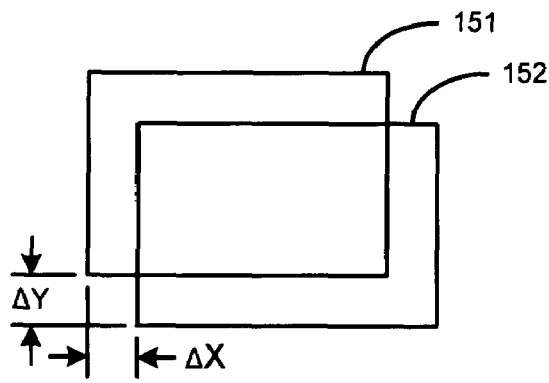
FIG. 15A illustrates in-plane translation in 2D-2D registration in one embodiment.
Figure 15B:
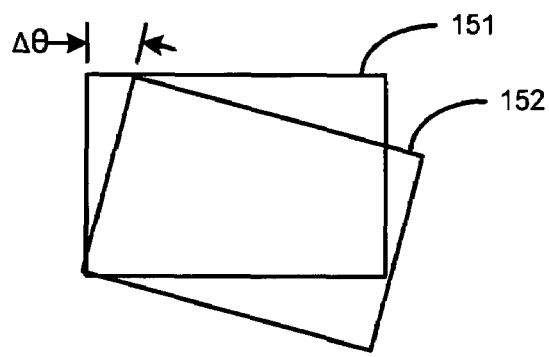
FIG. 15B illustrates in-plane rotation in 2D-2D registration in one embodiment.
Figure 15C:
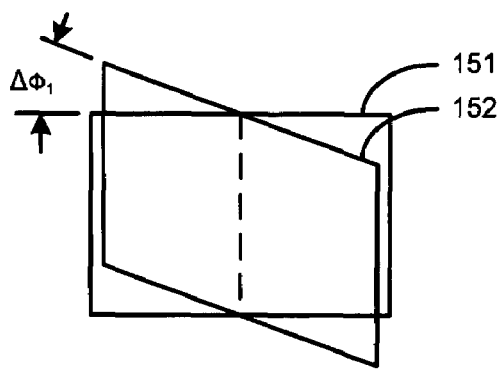
FIG. 15C illustrates a first out-of-plane rotation in 2D-2D registration in one embodiment.
Figure 15D:
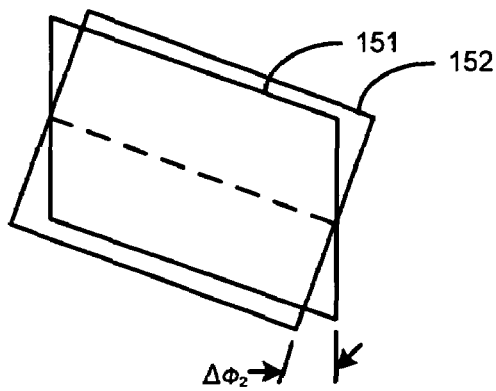
FIG. 15D illustrates a second out-of-plane rotation in 2D-2D registration in one embodiment.

FIG. 14 illustrates 3D transformation parameters between the 3D coordinate system $[X_P, Y_P, Z_P]$ of a patient in an imaging system having two 2D projections (such as x-ray imaging system 304) and a reference 3D coordinate system $[X_R, Y_R, Z_R]$ associated with a treatment plan derived from pre-treatment 3D scan data (in FIG. 14, the x-coordinates of both coordinate systems are normal to, and pointing into the plane of FIG. 14). Projections A and B in FIG. 14 are associated with the detectors in the imaging system (such as x-ray detectors 306) where $S_A$ and $S_B$ represent x-ray sources (such as x-ray sources 305). $O_A$ and $O_B$ are the centers of the imaging planes of the x-ray detectors. In FIG. 14, the projections A and B are viewed from the directions $O_A S_A$ and $O_B S_B$, respectively. These two 2D image projections are compared against DRRs to achieve image registration and/or alignment.

A 3D transformation may be defined from coordinate system $[X_P, Y_P, Z_P]$ (having coordinates x',y',z') to coordinate system $[X_R, Y_R, Z_R]$ (having coordinates x,y,z) in FIG. 14 in terms of three translations $(\Delta x, \Delta y, \Delta z)$ and three rotations $(\Delta\theta_x, \Delta\theta_y, \Delta\theta_z)$. A 3D rigid transformation between the two 3D coordinate systems can be derived from basic trigonometry as:

$$x=x', y=(y'-z')/\sqrt{2}, z=(y'+z')/\sqrt{2}, \theta_x=\theta_{x'}, \theta_y=(\theta_{y'}-\theta_{z'})/\sqrt{2}, \theta_z=(\theta_{y'}+\theta_{z'})/\sqrt{2}. \quad (1)$$

In the 2D coordinate system $(x_A, y_A)$ for projection A, the 3D rigid transformation may be decomposed into an in-plane transformation $(\Delta x_A, \Delta y_A, \Delta\theta_A)$ and two out-of-plane rotations $(\Delta\theta_{x_A}, \Delta\theta_{y'})$. Similarly, in the 2D coordinate system $(x_B, y_B)$ for projection B, the decomposition consists of the in-plane transformation $(\Delta x_B, \Delta y_B, \Delta\theta_B)$ and two out-of-plane rotations $(\Delta\theta_{x_B}, \Delta\theta_{z'})$. FIGS. 15A through 15D illustrate the in-plane transformations and out-of-plane rotations described herein, where a 2D x-ray image is represented by plane 151 and the 2D DRR is represented by plane 152. The 3D rigid transformation of equation (1) may be simplified by noting that the use of two projections over-constrains the solution to the six parameters of the 3D rigid transformation. The translation $x_A$ in projection A is the same parameter as $x_B$ in projection B, and the out-of-plane rotation $\theta_{x_A}$ in projection A is the same as $\theta_{x_B}$ in projection B. If $\alpha_A$ and $\alpha_B$ are geometric amplification factors (e.g., scale factors related to source-to-patient and patient-to-detector distances) for projections A and B, respectively, then the translations between the coordinate system [x'y'z'] and the 2D coordinate systems have the following relationships:

$$\Delta x' = (\alpha_B \Delta x_B - \alpha_A \Delta x_A)/2, \Delta y' = \alpha_A \Delta y_A, \Delta z' = \alpha_B \Delta y_B. \quad (2)$$

For projection A, given a set of DRR images that correspond to different combinations of the two out-of-plane rotations $(\Delta\theta_{x_A}, \Delta\theta_{y'})$, the 2D in-plane transformation $(\Delta x_A, \Delta y_A, \Delta\theta_A)$ may be estimated by a 2D to 2D image comparison, and the two out-of-plane rotations $(\Delta\theta_{x_A}, \Delta\theta_{y'})$ may be calculated by matching the x-ray image to the set of DRR images as described below, using similarity measures. Likewise, the same process may be used to solve the 2D in-plane transformation $(\Delta x_B, \Delta y_B, \Delta\theta_B)$ and the out-of-plane rotations $(\Delta\theta_{x_B}, \Delta\theta_{z'})$ for the projection B. As described below, the in-plane transformation and out-of-plane rotations may be obtained by registration between the x-ray image a DRR, independently for both projection A and projection B. When a DRR image with a matching out-of-plane rotation is identified, the in-plane rotation and the out-of-plane rotation have the following relationships:

$$\Delta\theta_{y'}=\Delta\theta_B, \Delta\theta_{z'}=\Delta\theta_A. \quad (3)$$

If the out-of-plane rotation $\theta_{y'}$ is ignored in the set of reference DRR images for projection A, the in-plane transformation can be approximately described by $(\Delta x_A, \Delta y_A, \Delta\theta_A)$ when $\theta_{y'}$ is small (e.g., less than 5°). Once this simplifying assumption is made, and given a set of reference DRR images which correspond to various out-of-plane rotations $\Delta\theta_{x_A}$, the in-plane transformation $(\Delta x_A, \Delta y_A, \Delta\theta_A)$ and the out-of-plane rotation $\Delta\theta_{x_A}$ may be found by one or more search methods as are known in the art. These methods generally employ the calculation of a similarity measure, followed by the application of a gradient search algorithm to maximize the similarity between the in-treatment x-ray images and selected DRRs. Examples of similarity measures include (but are not limited to) normalized cross-section, entropy of the difference image, mutual information, gradient correlation, pattern intensity and gradient difference. A corresponding simplification may be made for projection B.

Given the results $(\Delta x_A, \Delta y_A, \Delta\theta_A, \Delta\theta_{x_A})$ in projection A and $(\Delta x_B, \Delta y_B, \Delta\theta_B, \Delta\theta_{x_B})$ in projection B, the approximation of the 3D rigid transformation in the 3D image coordinate system may be obtained using the following expressions:

$$\Delta x=(-\alpha_A\Delta x_A+\alpha_B\Delta x_B)/2, \Delta y=(\alpha_A\Delta y_A-\alpha_B\Delta y_B)/\sqrt{2}, \Delta z=(\alpha_A\Delta y_A+\alpha_B\Delta y_B)/\sqrt{2}, \Delta\theta_x=(\Delta\theta_{x_A}+\Delta\theta_{x_B})/2, \Delta\theta_y=(\Delta\theta_B-\Delta\theta_A)/\sqrt{2}, \Delta\theta_z=(\Delta\theta_B+\Delta\theta_A)/\sqrt{2}. \quad (4)$$

Thus, the 3D transformation required to align the 3D coordinate system of the patient with the 3D coordinate system of a treatment plan may be completely defined by the two sets of four parameters $(\Delta x_A, \Delta y_A, \Delta\theta_A, \Delta\theta_{x_A})$ and $(\Delta x_B, \Delta y_B, \Delta\theta_B, \Delta\theta_{x_B})$.

Other ways of determining transformations as are known in the art are contemplated in one or more embodiments of the invention. In one embodiment, the 2D x-ray images in each projection of the x-ray imaging system may be combined for direct 2D-3D registration with the pre-operative 3D scan data as described in copending U.S. patent application Ser. No. 11/281,106. In other embodiments, patient pose may be varied in 3D space until a similarity metric between 2D images is optimized.

In a second phase of the operative procedure in one embodiment, the alignment phase, the patient positioning system 307 may be used to move the patient 310 through the computed 3D transformation to align the VOI with the reference position in the reference coordinate system $[X_R, Y_R, Z_R]$ at the imaging center OI (such that the residual transformation between the actual position of the patient and the reference position of the patient is less than some specified value). The process of imaging, computing a transformation and aligning the VOI may be iterated one or more times with the accuracy of each transformation improving with each iteration as the VOI gets closer to alignment with the reference position at the imaging center.

In an alternative embodiment, in place of aligning the VOI with the reference coordinate system at the imaging center, system 300 may store the 3D transformation parameters for future use as described below.

In one embodiment, tracking devices 313 may be fitted to the patient 310, for example, with an external vest or headgear or other attachment device as is known in the art. In one embodiment, three or more tracking devices may be used to define a 3D position of the patient in the imaging system 304 in a tracking coordinate system established by tracking system 311, which may be correlated with the patient position determined by the imaging system 304.

Tracking system 311 may be, for example, an optical, magnetic or electromagnetic tracking system as are known in the art. In an optical tracking system, for example, the tracking devices 313 may be light-emitting diodes and tracking apparatus 312 may be a 3D camera system that can locate the tracking devices in space. In a magnetic tracking system, for example, the tracking apparatus 312 may be a gradient magnetic field generator and the tracking devices 313 may be magnetic field detectors capable of sensing and reporting their locations in a gradient magnetic field. In an electromagnetic tracking system, for example, the tracking apparatus 312 may be a radio transceiver and the tracking devices 313 may be radio transponders capable of radio-location via phase comparison or time delay calculations using signals generated by the transceiver. Other tracking systems, devices and means for attaching such devices as are known in the art are contemplated embodiments of the present invention.

In one embodiment, the tracking system 311 may be calibrated to the treatment room coordinate system 314. In particular, the tracking system 311 may be programmed with the coordinates of the imaging center OI at the origin of the reference coordinate system $[X_R, Y_R, Z_R]$ in the imaging system 304 and with the coordinates of a treatment center $O_T$ at the origin of a reference coordinate system $[X'_R, Y'_R, Z'_R]$ in the radiation system 301, both of which may be known in the treatment room coordinate system 314. The difference between these two coordinate system origins (imaging center $O_I$ and treatment center $O_T$) may be expressed as a 3D difference vector between the imaging center $O_I$ and the treatment center $O_T$. The 3D difference vector may also be programmed into the patient positioning system 307.

In a third phase of the operative procedure in one embodiment, the transit phase, the patient positioning system 307 may use the 3D difference vector to move the patient 310 from the current position in the imaging system 304 to a position in the radiation system 301 as illustrated in FIG. 4. It will be appreciated that if the patient 310 has been pre-aligned with the reference coordinate system $[X_R, Y_R, Z_R]$ in the imaging system 304 at imaging center $O_I$, as described above, then the expected position of the VOI in the radiation system 301 will be in alignment with the reference coordinate system $[X'_R, Y'_R, Z'_R]$ at the treatment center $O_T$, provided that the patient 310 does not move on the treatment couch 308.

If the patient 310 has not been pre-aligned in the imaging system 304, then the expected position of the VOI (absent in-transit patient movement on the couch) will differ from alignment at the treatment center by the stored value of the 3D transformation described above, in which case the robotic arm 309 may be used to apply the 3D transformation to align the VOI with the reference coordinate system at the treatment center. Alternatively, if radiation system 301 has the capability (e.g., certain configurations of the CYBERKNIFE® Robotic Radiosurgery System manufactured by Accuray Incorporated of California), the radiation system 301 may compensate for the difference (i.e., the 3D transformation) between the position of the VOI and the reference position at the treatment center.

The tracking system 311 may be used to detect patient movement in the radiation system by recording the positions of the tracking devices 313 in the radiation system 301, immediately after the transit, and monitoring their positions in the radiation system during the radiation treatment. The tracking system may also be used to determine if the patient has moved on the treatment couch during the transit by comparing the positions of the tracking devices in the imaging system before the transit with their position in the radiation system immediately after the transit. If the difference between the two positions deviates from the known difference vector between the treatment center $O_T$ and the imaging center $O_I$, then the system knows that the patient has moved on the couch.

Figure 12:
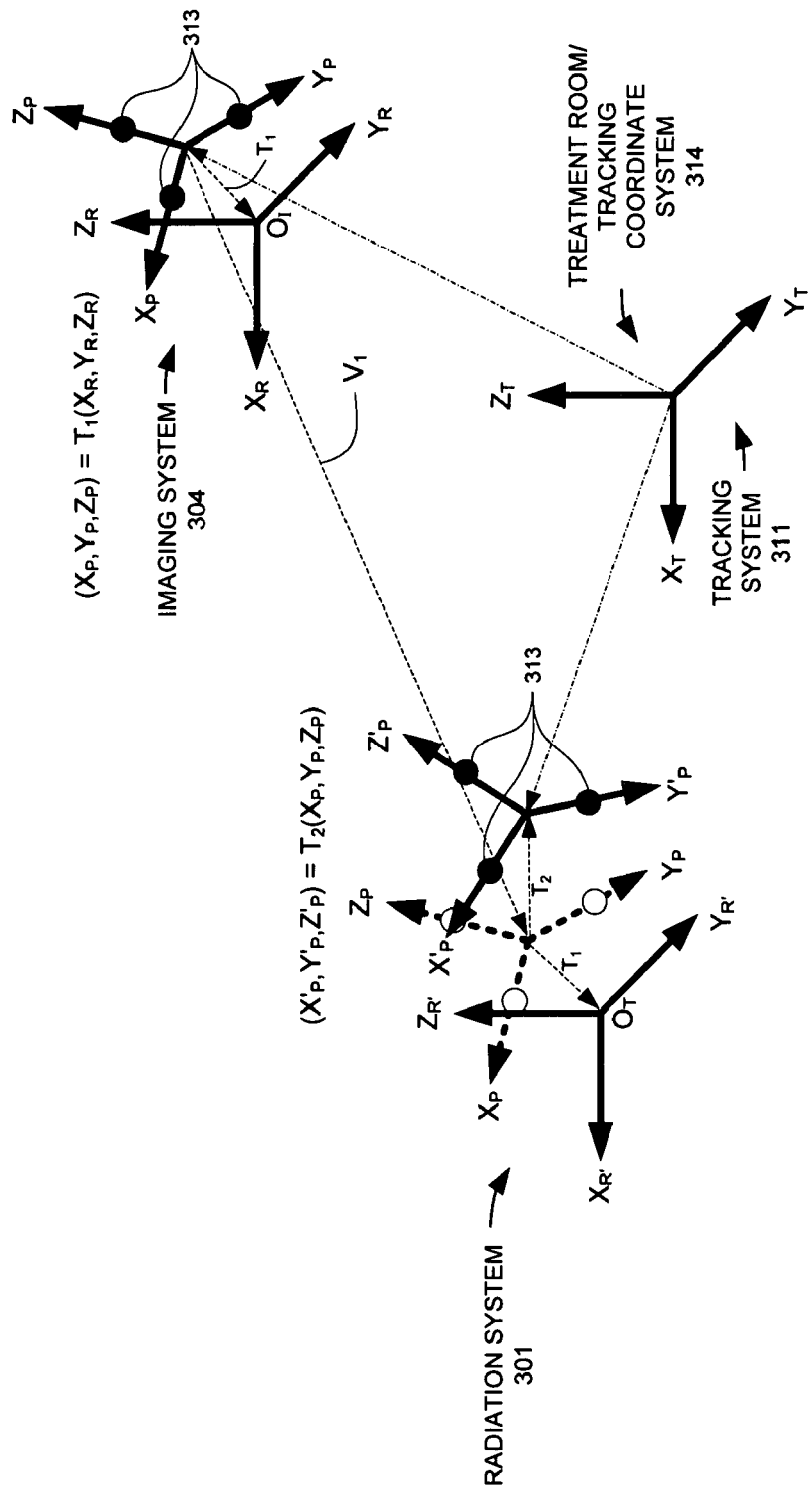
FIG. 12 illustrates target tracking in one embodiment.

FIG. 12 illustrates the above described coordinate systems, alignments, transformations and transit symbolically. In FIG. 12, coordinate system $[X_T,Y_T,Z_T]$ is the treatment room/tracking coordinate system 314, to which all other coordinates are referenced. Coordinate system $[X_R,Y_R,Z_R]$ is the reference coordinate system of imaging system 304 with an origin at imaging center $O_I$. Coordinate system $[X_P,Y_P,Z_P]$ represents the position of the VOI in the imaging system 304. The locations of the tracking devices 313 are shown as aligned with the axes of the patient coordinate system for convenience of illustration only (in general, the locations of the tracking devices may be defined by another 3D transformation with respect to the patient coordinate system). The 3D transformation between the imaging reference coordinate system $[X_R,Y_R,Z_R]$ and the patient coordinate system $[X_P,Y_P,Z_P]$ is represented by the operator $T_1$.

Coordinate system $[X'_R,Y'_R,Z'_R]$ is the reference coordinate system of radiation system 301 with an origin at treatment center $O_T$. Vector $V_1$ is the difference vector between $O_T$ and $O_I$. As illustrated in FIG. 12, if the VOI (represented by patient coordinates $[X_P,Y_P,Z_P]$) is translated over the difference vector $V_1$ by the positioning system 307, and the patient 310 does not move relative to the treatment couch 308, the expected position of the VOI (shown as the dashed line coordinate system $[X_P,Y_P,Z_P]$), relative to the treatment coordinate system $[X'_R,Y'_R,Z'_R]$ can be represented by the transformation operator $T_1$. However, if the patient 310 does move on the treatment couch 308, then the tracked position of the VOI (represented by the $[X'_P,Y'_P,Z'_P]$ coordinate system) will differ from the expected position by an additional transformation operator $T_2$, which can be determined by the tracking system by locating the tracking devices 313 in the treatment system 301. It will be appreciated that if the VOI is pre-aligned in the imaging system 304, then the value of $T_1$ will be approximately zero, depending on the accuracy of the alignment algorithm and the number of alignment iterations performed in the imaging system.

Following the transit phase, several options are possible during the radiation treatment phase. If the patient 310 moves or has moved less then a specified maximum amount (i.e., the VOI is close to its expected position), then the patient positioning system 307 (or the radiation system 301) may be used to align the VOI with the reference coordinate system $[X'_R, Y'_R,Z'_R]$ at the treatment center $O_T$, and treatment may begin. If the patient has moved by more than the specified maximum amount, then the tracking system 311 may sound an alarm and/or signal the radiation system 301 to halt. In one embodiment, the positioning system 307 may move the patient 310 back to the imaging system 304 (e.g., using the inverse of the 3D difference vector) for re-alignment in the imaging system as described above.

Once treatment has started, the tracking system 311 may be used to continuously monitor patient position with respect to the aligned patient position in the radiation system 301 and to generate an alarm or to halt treatment if the position of the VOI changes by less a specified maximum amount. As described above, the VOI may then be re-aligned in the radiation system 301. If the movement of the VOI is greater than the specified amount, the VOI maybe returned to the imaging system 304 for re-alignment there.

Figure 9:
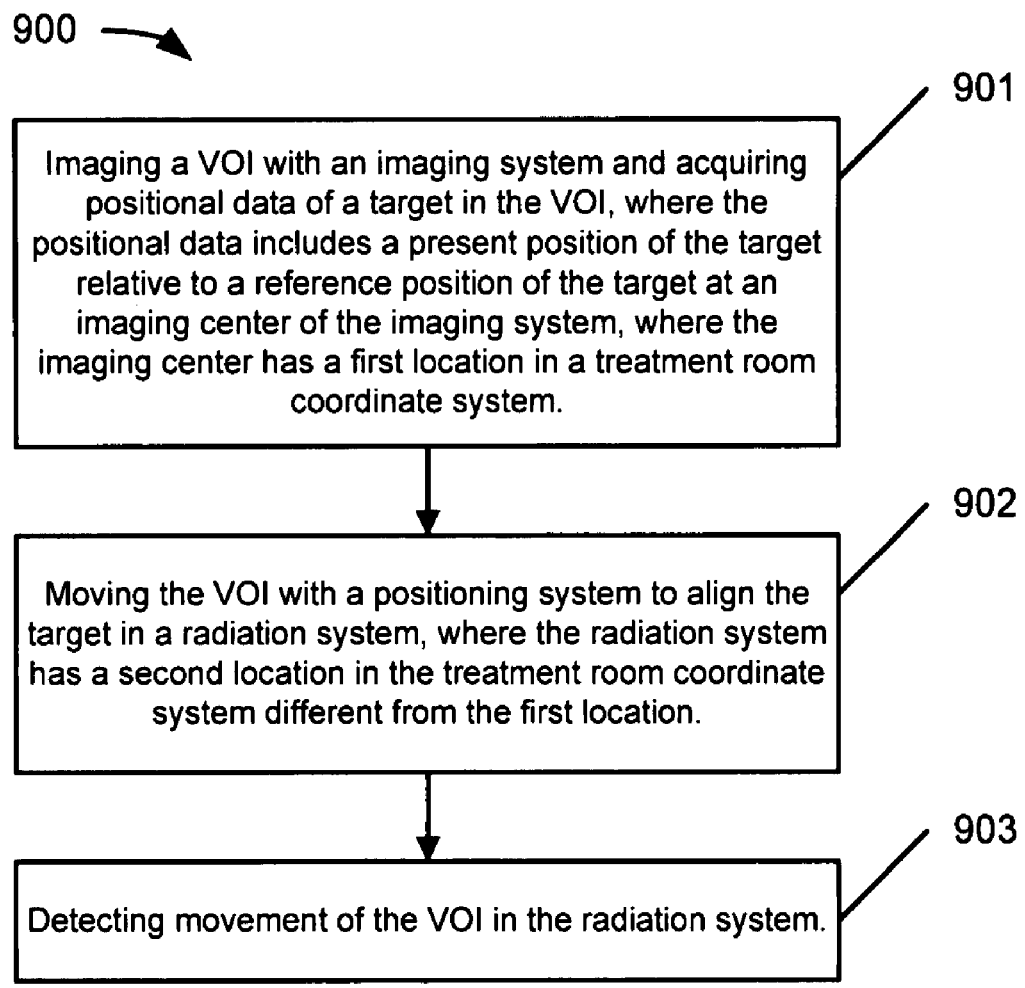
FIG. 9 is a flowchart illustrating a method in one embodiment.

FIG. 9 is a flowchart illustrating a method 900 in one embodiment of the present invention. Method 900 includes imaging a volume of interest (VOI) with an imaging system and acquiring positional data of a target within the VOI, where the positional data comprises a present position of the target relative to a reference position of the target at an imaging center of the imaging system, wherein the imaging center has a first location in a treatment room coordinate system (operation 901). Method 900 also includes moving the VOI with a positioning system, to align the target in a radiation system, where the radiation treatment center has a second location in the treatment room coordinate system different from the first location (operation 902), and treating the target at the second location (operation 903).

Figure 10A:
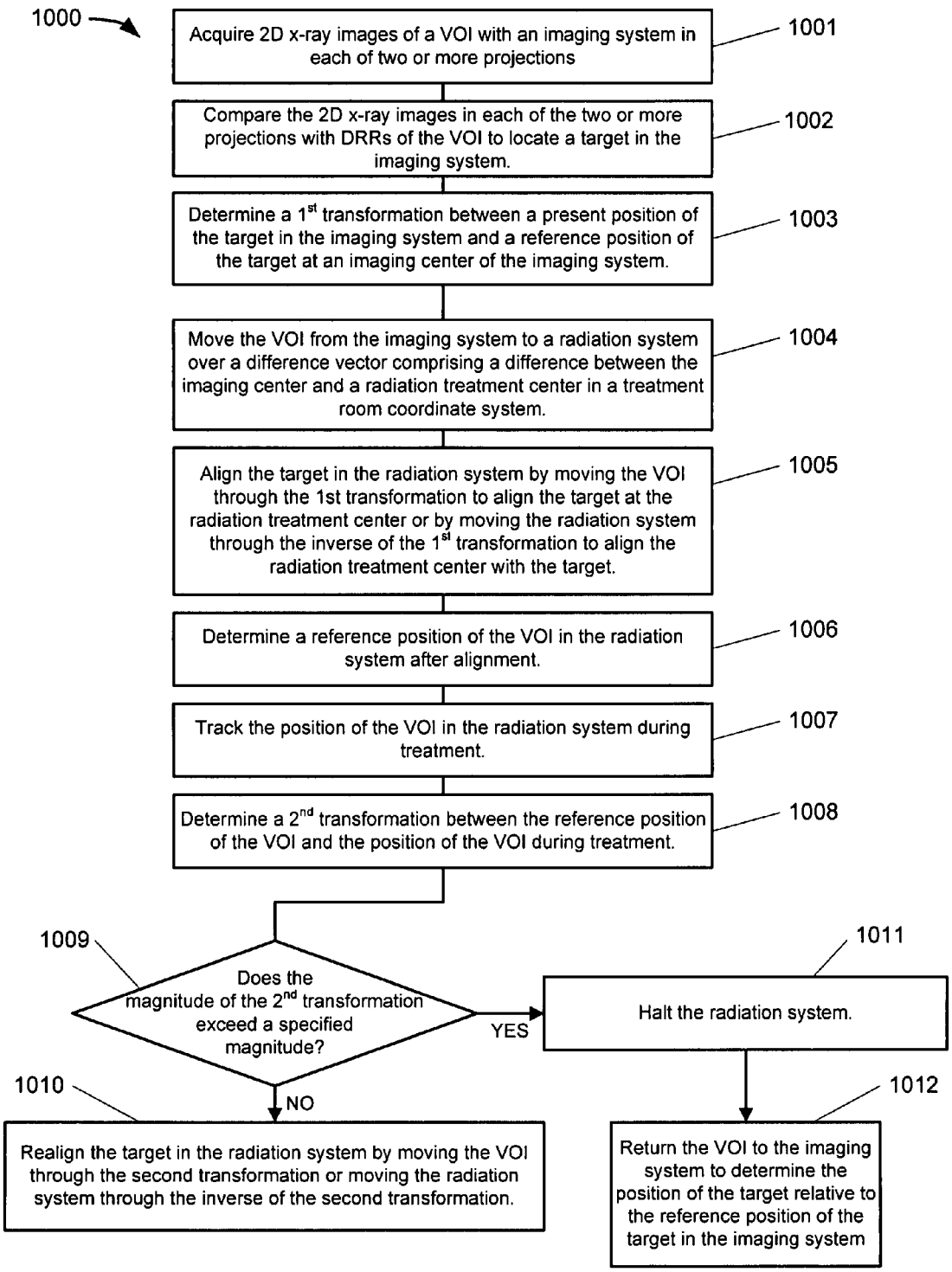
FIG. 10A is a flowchart illustrating a method in another embodiment.

In one embodiment, as illustrated in by the flowchart of FIG. 10A and with reference to FIGS. 3 and 4, a method 1000 includes acquiring 2D x-ray images of a VOI with an imaging system (e.g., imaging system 304) in each of two or more projections (operation 1001); comparing the 2D x-ray images in each of the two or more projections with DRRs of the VOI to locate a target in the imaging system (operation 1002); and determining a first transformation comprising a 3D transformation between a present position of the target in the imaging system and a reference position of the target at an imaging center (e.g., imaging center $O_I$) of the imaging system (operation 1003).

Method 1000 may also include moving the VOI from the imaging system to a radiation system (e.g., radiation system 301) over a difference vector comprising a difference between the imaging center and a radiation treatment center (e.g., radiation treatment center $O_T$ in radiation system 301) in a treatment room coordinate system (operation 1004); aligning the target in the radiation system by moving the VOI through the first transformation to align the target at the radiation treatment center or by moving the radiation system to align the radiation treatment center with the target (operation 1005); determining a reference position of the VOI in the radiation system after the alignment (operation 1006); tracking the position of the VOI (e.g., with tracking system 312) in the radiation system during treatment (operation 1007); and determining a second transformation comprising a 3D transformation between the reference position of the VOI and the position of the VOI during treatment (operation 1008).

If the magnitude of the second transformation does not exceed a specified magnitude at operation 1009, then the method continues by realigning the target in the radiation system by moving the VOI through the second transformation (e.g., with the positioning system 307) or moving the radiation system through the inverse of the second transformation (operation 1010). If the magnitude of the second transformation does exceed the specified magnitude at operation 1009, then the method continues by halting the radiation system (operation 1011) and returning the VOI to the imaging system to determine the position of the target relative to the reference position of the target in the imaging system (operation 1012).

Figure 7:
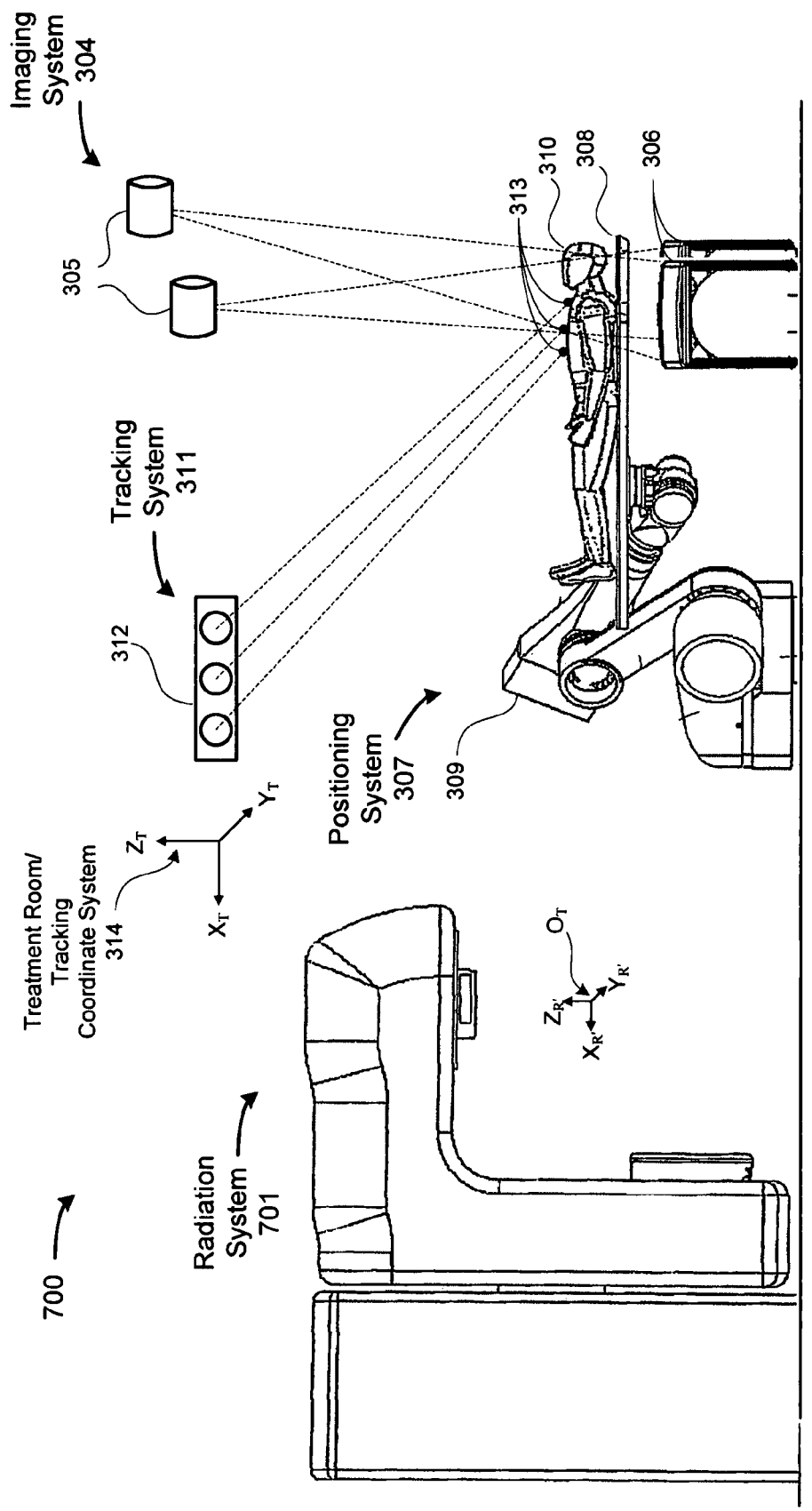
FIG. 7 illustrates another image-guided radiation treatment system in a first configuration in one embodiment.
Figure 8:
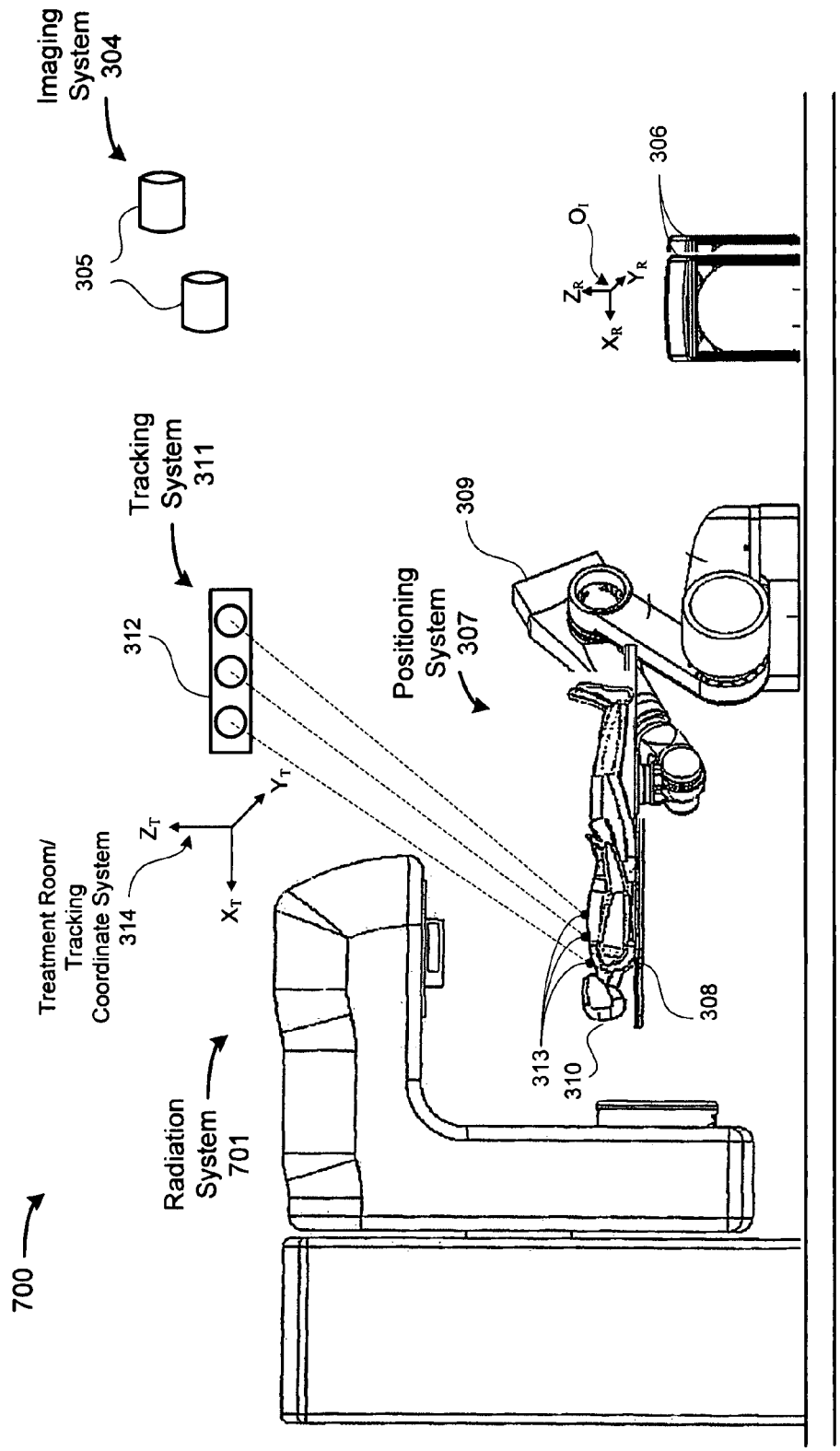
FIG. 8 illustrates the image-guided radiation treatment system of FIG. 7 in a second configuration in one embodiment.
Figure 10B:
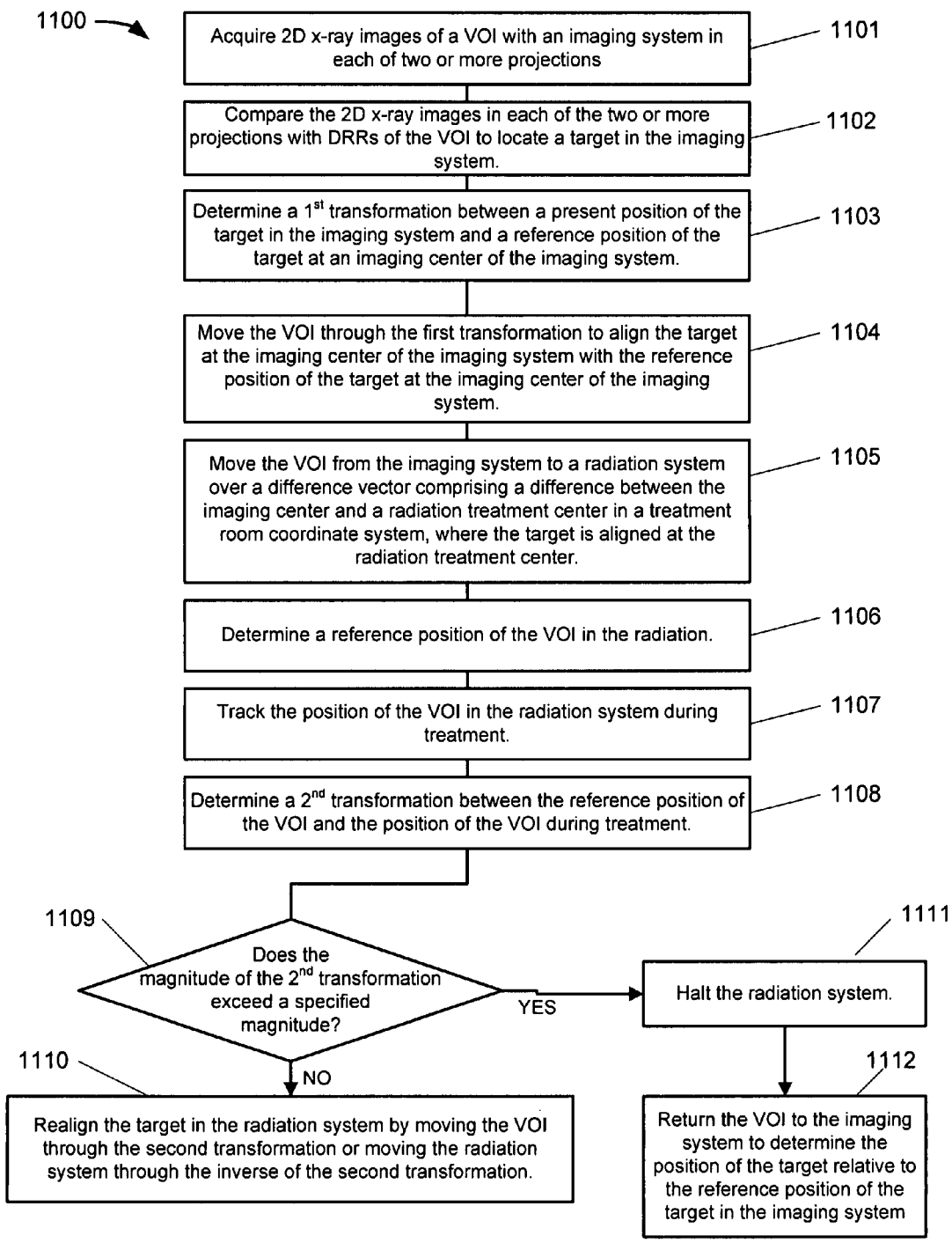
FIG. 10B is a flowchart illustrating a method in another embodiment.

In another embodiment, as illustrated in FIGS. 7 and 8, an image-guided radiation treatment system 700 may include a gantry-based radiation system 701 instead of the robotic radiation system illustrated in FIGS. 3 and 4. In one embodiment, as illustrated by the flowchart of FIG. 10B and with reference to FIGS. 7 and 8, a method 1100 includes acquiring 2D x-ray images of a VOI with an imaging system (e.g., imaging system 304) in each of two or more projections (operation 1101); comparing the 2D x-ray images in each of the two or more projections with DRRs of the VOI to locate a target in the imaging system (operation 1102); and determining a first transformation comprising a 3D transformation between a present position of the target in the imaging system and a reference position of the target at an imaging center (e.g., imaging center OI) of the imaging system (operation 1103).

Method 1100 may include moving the VOI through the first transformation to align the target at the imaging center with the reference position of the target at the imaging center (operation 1104); and moving the VOI from the imaging system to a radiation system (e.g., radiation system 701) over a difference vector comprising a difference between the imaging center and a radiation treatment center (e.g., radiation treatment center OT in radiation system 701) in a treatment room coordinate system, where the target is aligned at the radiation treatment center (operation 1105).

Method 1100 may also include determining a reference position of the VOI in the radiation system (e.g., with tracking system 312) after operation 1105 is completed (operation 1106); tracking the position of the VOI in the radiation system during treatment (operation 1107); and determining a second transformation comprising a 3D transformation between the reference position of the VOI and the position of the VOI during treatment (operation 1108).

If the magnitude of the second transformation does not exceed a specified magnitude at operation 1109, then the method continues by realigning the target in the radiation system by moving the VOI through the second transformation (e.g., with the positioning system 307) (operation 1110). If the magnitude of the second transformation does exceed the specified magnitude at operation 1109, then the method continues by halting the radiation system (operation 1111) and returning the VOI to the imaging system to determine the position of the target relative to the reference position of the target in the imaging system (operation 1112). It will be appreciated that method 1100 may also be implemented in system 300.

Figure 5:
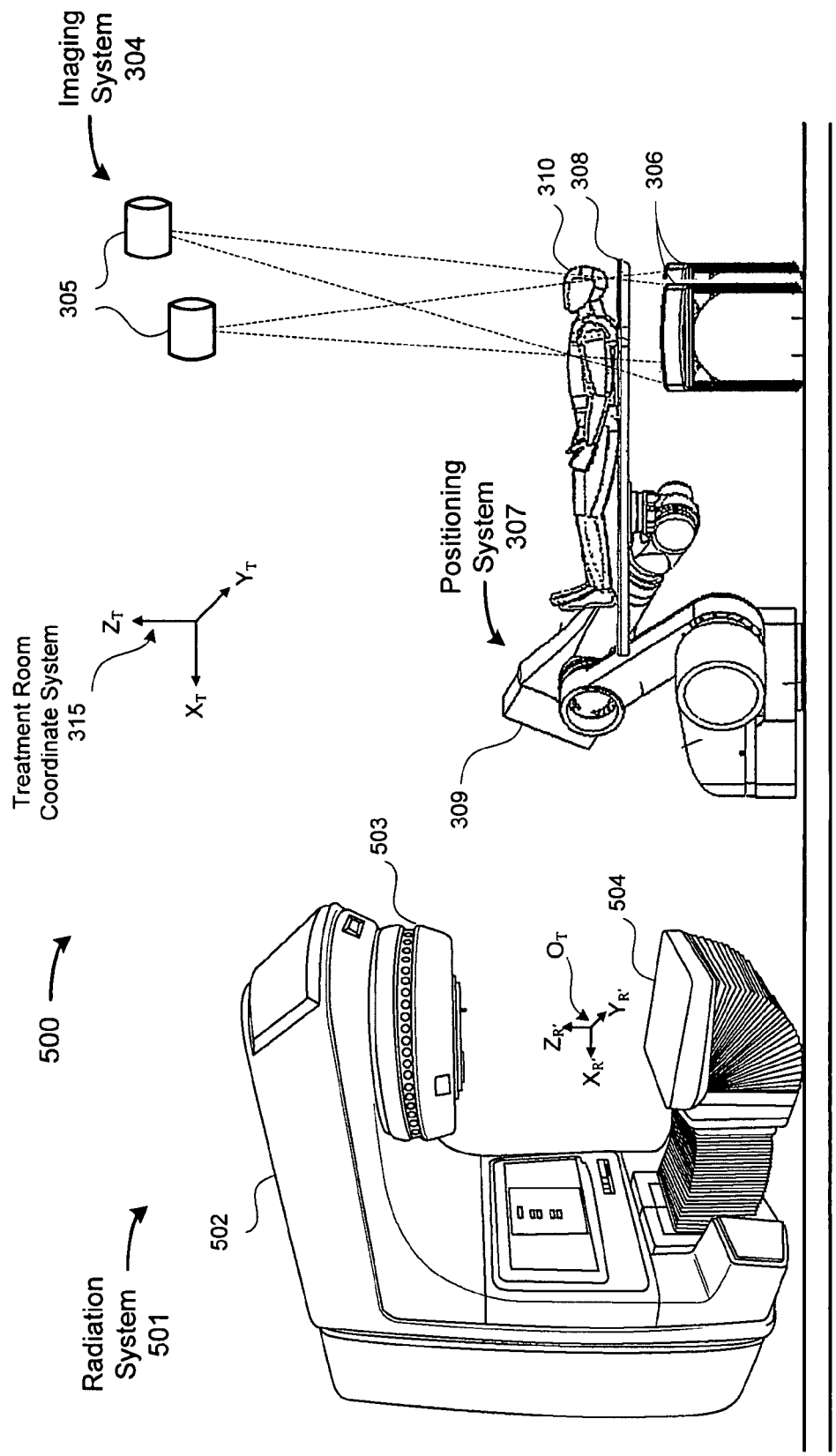
FIG. 5 illustrates another image-guided radiation treatment system in a first configuration in one embodiment.
Figure 6:
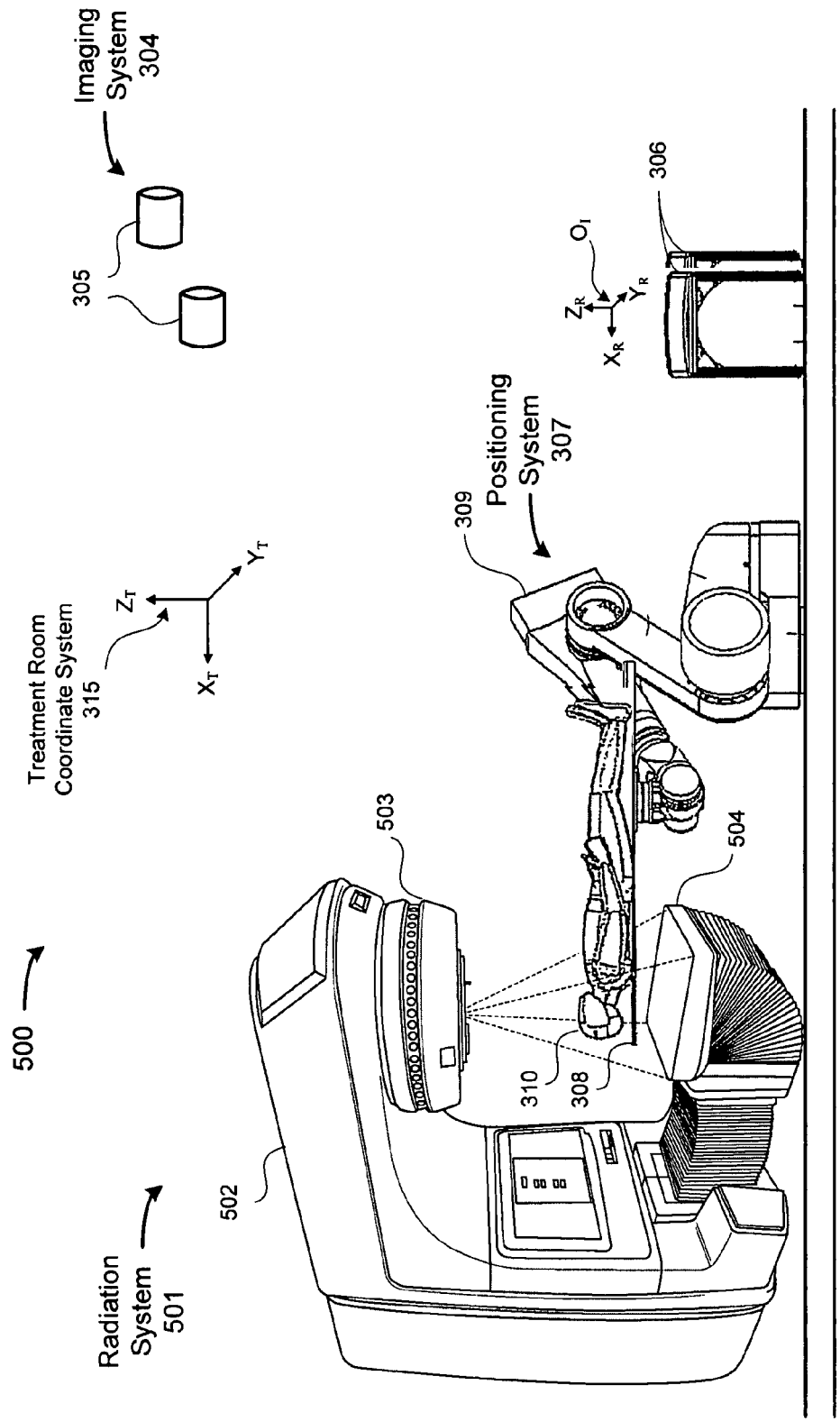
FIG. 6 illustrates the image-guided radiation treatment system of FIG. 5 in a second configuration in one embodiment.

FIGS. 5 and 6 illustrate an image-guided radiation treatment system 500 in one embodiment which includes imaging system 304 and a treatment delivery system including patient positioning system 307 and a gantry-based radiation system 501 having a gantry 502, a radiation source 503 and a portal imaging device 504.

As illustrated in FIG. 5, in the imaging and registration phase of the operative procedure, the patient 310 is placed on the treatment couch 308. The positioning system 307 may be used to move the patient such that the VOI is positioned in the field of view of the x-ray imaging system 304 in proximity to the center of the x-ray imaging system (imaging center OI), which has known coordinates in a treatment room coordinate system. While the patient is positioned in the imaging system 304, 2D x-ray images of the VOI (including the defined radiation treatment target) may be captured by the imaging system 304. The 2D x-ray images may be registered with one or more 2D reference DRRs of the VOI in each projection of the x-ray imaging system 304, as described above, and used to determine a 3D transformation between the position of the patient in the imaging system (represented by the live x-ray images) and a reference position of the patient (represented by the DRRs) associated with the treatment plan.

In the alignment phase of the operative procedure, the patient positioning system 307 may be used to move the patient 310 through the computed 3D transformation to align the VOI with the reference position in the reference coordinate system [XR,YR,ZR] at the imaging center OI (such that the residual transformation between the actual position of the patient and the reference position of the patient is less than some specified value). Once the patient is aligned in the imaging system 304, reference x-rays in one or more projections may be acquired and transferred to the radiation system 501 for use as described below.

In one embodiment, the patient positioning system 307 may be calibrated to the treatment room coordinate system 315. In particular, the patient positioning system 307 may be programmed with the coordinates of the imaging center $O_I$ at the origin of the reference coordinate system $[X_R,Y_R,Z_R]$ in the imaging system 304. Patient positioning system 307 may also be programmed with the coordinates of a treatment isocenter OT at the origin of a reference coordinate system $[X'_R,Y'_R,Z'_R]$ in the radiation system 501. As described above, the difference between these two coordinate system origins (imaging center $O_I$ and treatment isocenter $O_T$) may be expressed as a 3D difference vector between the imaging center $O_I$ and the treatment isocenter $O_T$. The 3D difference vector may also be programmed into the patient positioning system 307.

In the transit phase of the operative procedure, the patient positioning system 307 may use the 3D difference vector to move the patient 310 from the current position in the imaging system 304 to a position in the radiation system 501 as illustrated in FIG. 6. It will be appreciated that if the patient 310 has been pre-aligned with the reference coordinate system $[X_R,Y_R,Z_R]$ in the imaging system 304 at imaging center $O_I$, as described above, then the expected position of the VOI in the radiation system 501 will be in alignment with the reference coordinate system $[X'_R,Y'_R,Z'_R]$ at the treatment isocenter $O_T$, provided that the patient 310 has not moved on the treatment couch 308 during the transit from the imaging system 304 to the radiation system 501.

Figure 13:
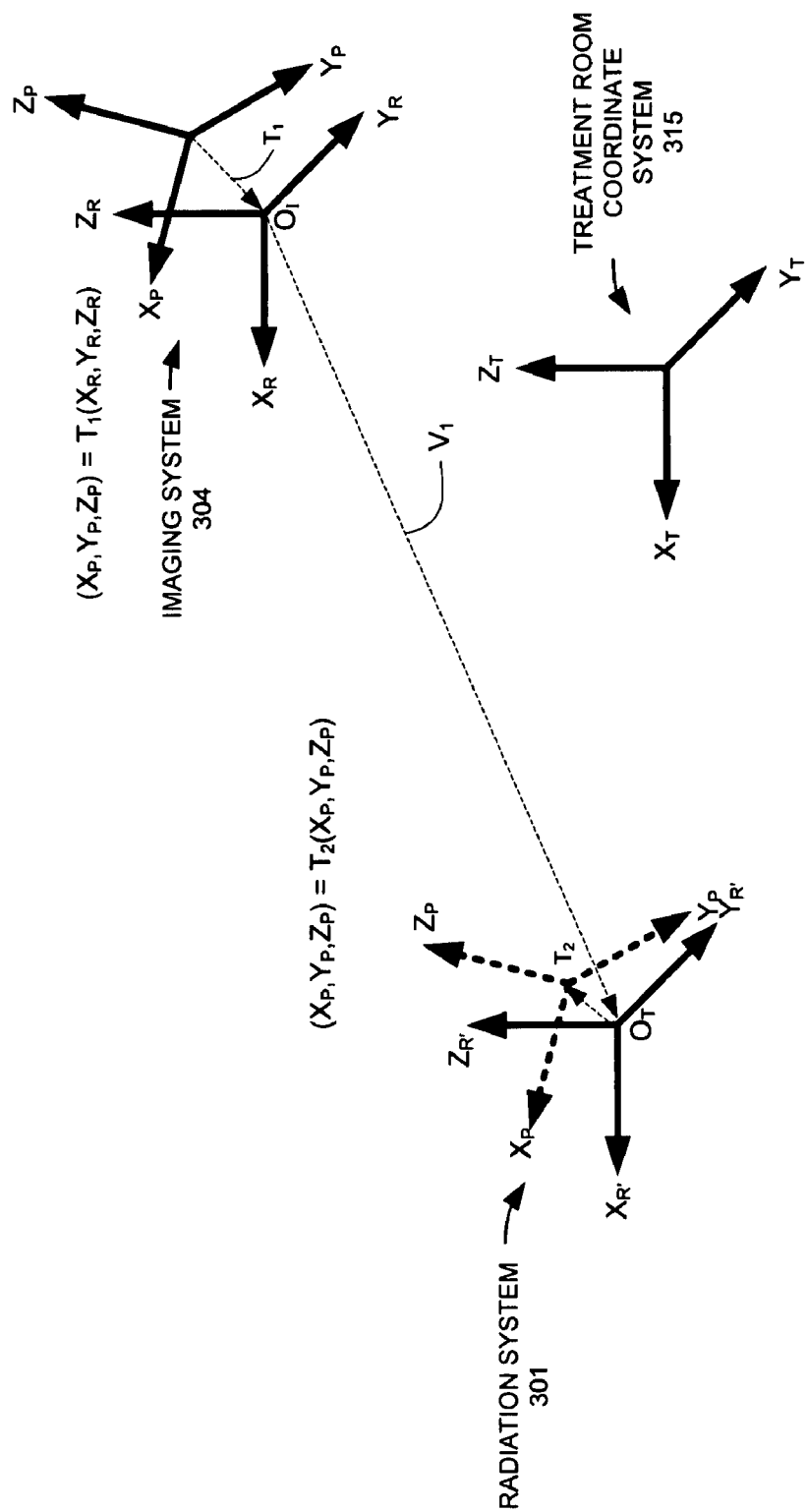
FIG. 13 illustrates target tracking in another embodiment.

FIG. 13 illustrates the above described coordinate systems, alignments, transformations and transit symbolically. In FIG. 13, coordinate system 315 $[X_T,Y_T,Z_T]$ is the treatment room coordinate system, to which all other coordinates are referenced. Coordinate system $[X_R,Y_R,Z_R]$ is the reference coordinate system of imaging system 304 with an origin at imaging center $O_I$. Coordinate system $[X_P,Y_P,Z_P]$ represents the initial position of the VOI in the imaging system 304. The 3D transformation between the imaging reference coordinate system $[X_R,Y_R,Z_R]$ and the patient coordinate system $[X_P,Y_P,Z_P]$ is represented by the operator $T_1$.

Coordinate system $[X'_R,Y'_R,Z'_R]$ is the reference coordinate system of the radiation system 501 with an origin at treatment isocenter $O_T$. Vector $V_1$ is the difference vector between $O_T$ and $O_I$. As illustrated in FIG. 13, if the VOI (represented by patient coordinates $[X_P,Y_P,Z_P]$) is pre-aligned at imaging center $O_I$ with transformation $T_1$, and then translated over the difference vector $V_1$ by the positioning system 307 (and the patient 310 does not move relative to the treatment couch 308), the VOI (shown as the dashed line coordinate system $[X_P,Y_P,Z_P]$) will be approximately aligned in the treatment coordinate system $[X'_R,Y'_R,Z'_R]$. However, if the patient 310 does move on the treatment couch 308, then the position of the VOI will differ from the position by a transformation operator $T_2$.

In one embodiment, the gantry 502 of radiation system 501 may be rotated to an angle corresponding to a selected projection of the imaging system 304 and used to acquire a 2D portal image of the VOI corresponding to the selected projection. The 2D portal image may then be compared with the reference x-ray image of the VOI in the same projection with the patient aligned in the imaging system 304. As illustrated in FIG. 15, the 2D-2D comparison (i.e., portal image to reference x-ray) may be used to determine if the patient has moved with respect to the reference alignment position, because in-plane and out-of-plane rotations, and in-plane translations, between the reference x-ray and the portal image will produce differences between the portal image and the x-ray image.

It will be appreciated that while, generally, two images from different projections are required for stereotactic positioning, one image can be used for assessment of motion. In some cases, patient movement may be quantified using only a single image. For example, if the patient has only rotated in the axis of rotation of radiation system 501, the amount of rotation can be detected by capturing additional portal images at different projection angles until the portal image and the reference x-ray image are adequately matched. The patient positioning system 307 may then be used to conform the position of the patient in the treatment system to the reference position of the patient as aligned in the imaging system.

In general, however, the 2D-2D comparison may be used to detect movement thresholds. If the detected level of patient movement exceeds a specified threshold magnitude, the radiation system 501 may be halted and the patient positioning system may be used to return the patient to the imaging system 30 for re-alignment of the VOI as described above.

Once treatment has started, portal imaging may be used periodically during treatment to monitor patient movement in the radiation system 501 and to generate an alarm or to halt treatment if the movement of the VOI exceeds the specified threshold. As described above, the VOI may then be returned to the imaging system 304 for re-alignment there.

Figure 10C:
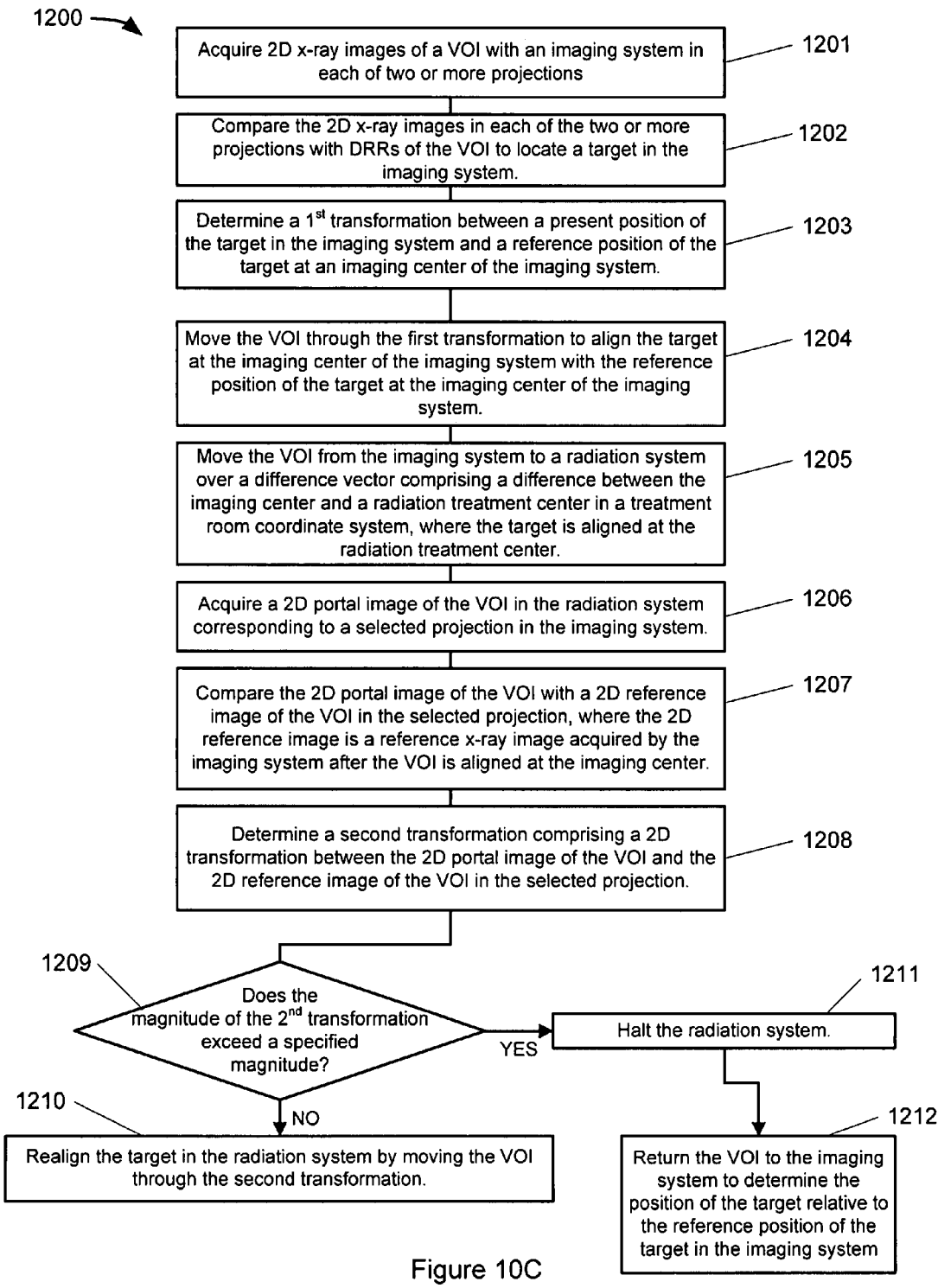
FIG. 10C is a flowchart illustrating a method in another embodiment.

In one embodiment, as illustrated in by the flowchart of FIG. 10C and with reference to FIGS. 5 and 6, a method 1200 includes acquiring 2D x-ray images of a VOI with an imaging system (e.g., imaging system 304) in each of two or more projections (operation 1201); comparing the 2D x-ray images in each of the two or more projections with DRRs of the VOI to locate a target in the imaging system (operation 1202); and determining a first transformation comprising a 3D transformation between a present position of the target in the imaging system and a reference position of the target at an imaging center (e.g., imaging center OI) of the imaging system (operation 1203).

Method 1200 may also include moving the VOI through the first transformation to align the target at the imaging center with the reference position of the target at the imaging center (operation 1104); and moving the VOI from the imaging system to a radiation system (e.g., radiation system 501) over a difference vector comprising a difference between the imaging center and a radiation treatment center (e.g., radiation treatment center OT in radiation system 501) in a treatment room coordinate system, where the target is aligned at the radiation treatment center (operation 1205).

Method 1200 may also include acquiring a 2D portal image of the VOI in the radiation system corresponding to a selected projection in the imaging system (operation 1206); comparing the 2D portal image of the VOI with a 2D reference image of the VOI in the selected projection, where the 2D reference image is a reference x-ray image acquired by the imaging system after the target is aligned with the reference position of the target in the imaging system in operation 1205 (operation 1207); and determining a second transformation comprising a 2D transformation between the 2D portal image of the VOI and the 2D reference image of the VOI in the selected projection (operation 1208).

If the magnitude of the second transformation does not exceed a specified magnitude at operation 1209, then the method continues by realigning the target in the radiation system by moving the VOI through the second transformation (e.g., with the positioning system 307) (operation 1210). If the magnitude of the second transformation does exceed the specified magnitude at operation 1209, then the method continues by halting the radiation system (operation 1211) and returning the VOI to the imaging system to determine the position of the target relative to the reference position of the target in the imaging system (operation 1212).

Figure 11:
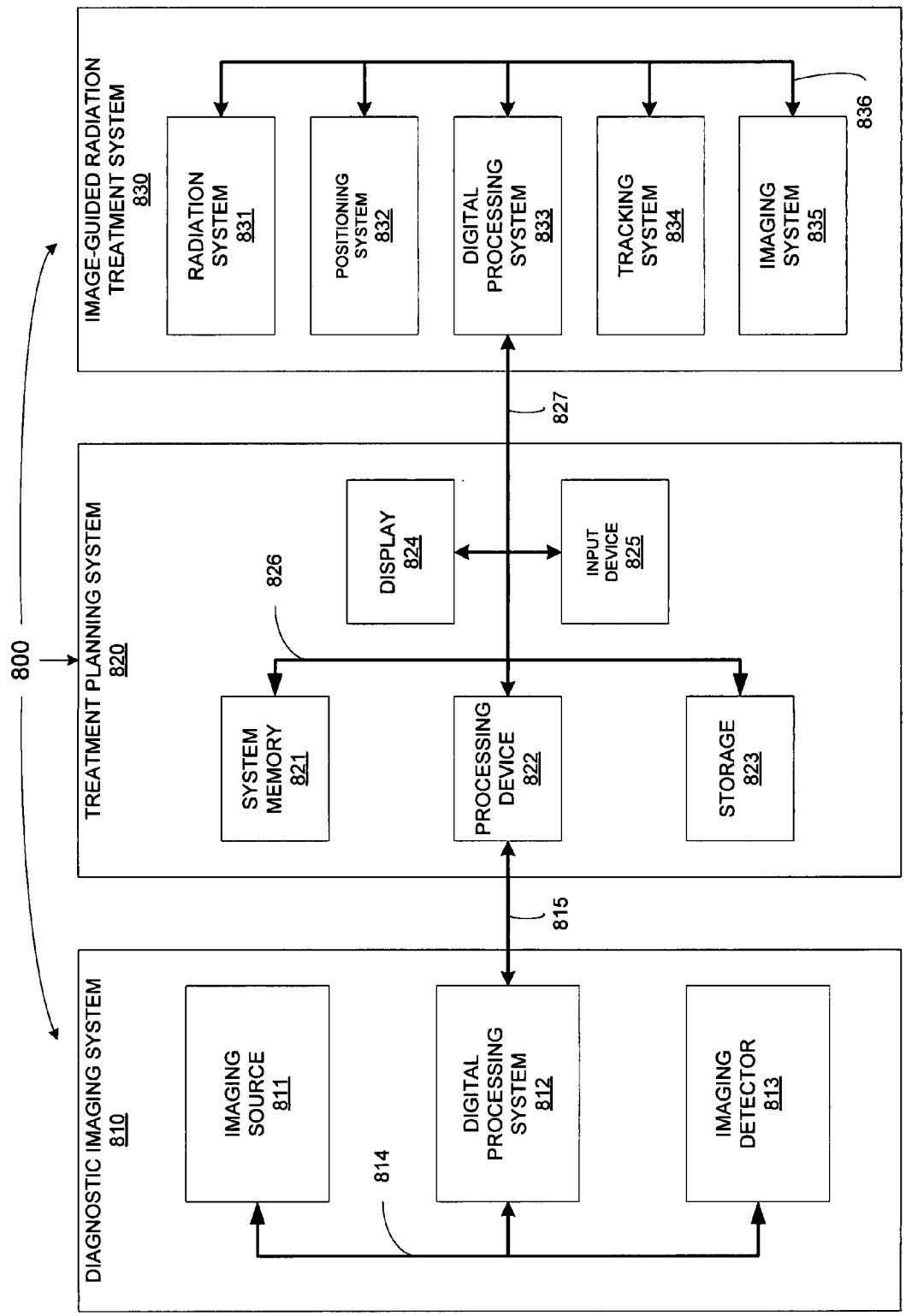
FIG. 11 is a block diagram illustrating a system in which embodiments of the invention may be practiced.

FIG. 11 illustrates one embodiment of a system 800 that may be used in performing radiation treatment in which embodiments of the present invention may be implemented. As described below and illustrated in FIG. 11, system 800 may include a diagnostic imaging system 810, a treatment planning system 820 and an image-guided radiation treatment system 830.

Diagnostic imaging system 810 may be any system capable of producing medical diagnostic images of a patient that may be used for subsequent medical diagnosis, treatment planning and/or treatment delivery. For example, diagnostic imaging system 810 may be a computed tomography (CT) system, a magnetic resonance imaging (MRI) system, a positron emission tomography (PET) system, an ultrasound system or the like. For ease of discussion, diagnostic imaging system 810 may be discussed at times in relation to a CT imaging modality. However, other imaging modalities such as those above may also be used.

Diagnostic imaging system 810 includes an imaging source 811 to generate an imaging beam (e.g., x-rays, ultrasonic waves, radio frequency waves, etc.) and an imaging detector 813 to detect and receive the beam generated by imaging source 811, or a secondary beam or emission stimulated by the beam from the imaging source (e.g., in an MRI or PET scan). Imaging source 811 and imaging detector 813 may be capable of rotation and/or translation with respect to a diagnostic volume of interest to generate 3D scan data. In one embodiment, diagnostic imaging system 810 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, may also be used that would be illuminated by each x-ray imaging source. Alternatively, other numbers and configurations of imaging sources and imaging detectors may be used.

The imaging source 811 and the imaging detector 813 may be coupled to a digital processing system 812 to control the imaging operation and process image data. Diagnostic imaging system 810 includes a bus or other means 814 for transferring data and commands among digital processing system 812, imaging source 811 and imaging detector 813. Digital processing system 812 may include one or more general-purpose processors (e.g., a microprocessor), special purpose processor such as a digital signal processor (DSP) or other type of device such as a controller or field programmable gate array (FPGA). Digital processing system 812 may also include other components (not shown) such as memory, storage devices, network adapters and the like. Digital processing system 812 may be configured to generate digital diagnostic images in a standard format, such as the DICOM (Digital Imaging and Communications in Medicine) format, for example. In other embodiments, digital processing system 812 may generate other standard or non-standard digital image formats. Digital processing system 812 may transmit diagnostic image files (e.g., the aforementioned DICOM formatted files) to treatment planning system 820 over a data link 815, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 820 includes a processing device 822 to receive and process image data. Processing device 822 may represent one or more general-purpose processors (e.g., a microprocessor), special purpose processor such as a digital signal processor (DSP) or other type of device such as a controller or field programmable gate array (FPGA). Processing device 822 may be configured to execute instructions for performing treatment planning and/or image processing operations discussed herein, such as the spine segmentation tool described herein.

Treatment planning system 820 may also include system memory 821 that may include a random access memory (RAM), or other dynamic storage devices, coupled to processing device 822 by bus 826, for storing information and instructions to be executed by processing device 822. System memory 821 also may be used for storing temporary variables or other intermediate information during execution of instructions by processing device 822. System memory 821 may also include a read only memory (ROM) and/or other static storage device coupled to bus 826 for storing static information and instructions for processing device 2010.

Treatment planning system 820 may also include storage device 823, representing one or more storage devices (e.g., a magnetic disk drive or optical disk drive) coupled to bus 826 for storing information and instructions. Storage device 823 may be used for storing instructions for performing the treatment planning steps discussed herein and/or for storing 3D imaging data and DRRs as discussed herein.

Processing device 822 may also be coupled to a display device 824, such as a cathode ray tube (CRT) or liquid crystal display (LCD), for displaying information (e.g., a 2D or 3D representation of the VOI) to the user. An input device 825, such as a keyboard, may be coupled to processing device 822 for communicating information and/or command selections to processing device 822. One or more other user input devices (e.g., a mouse, a trackball or cursor direction keys) may also be used to communicate directional information, to select commands for processing device 822 and to control cursor movements on display 824.

It will be appreciated that treatment planning system 820 represents only one example of a treatment planning system, which may have many different configurations and architectures, which may include more components or fewer components than treatment planning system 820 and which may be employed with the present invention. For example, some systems often have multiple buses, such as a peripheral bus, a dedicated cache bus, etc. The treatment planning system 820 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 820 may share its database (e.g., data stored in storage device 823) with a treatment delivery system, such as treatment delivery system 830. Treatment planning system 820 may be linked to treatment delivery system 830 via a data link 827, which may be a direct link, a LAN link or a WAN link as discussed above with respect to data link 815. It should be noted that when data links 815 and 827 are implemented as LAN or WAN connections, any of diagnostic imaging system 810, treatment planning system 820 and/or treatment delivery system 830 may be in decentralized locations such that the systems may be physically remote from each other. Alternatively, any of diagnostic imaging system 810, treatment planning system 820 and/or treatment delivery system 830 may be integrated with each other in one or more systems.

Treatment delivery system 830 includes a therapeutic and/or surgical radiation system 831 to administer a prescribed radiation dose to a radiation target in conformance with a treatment plan, an imaging system 835 to capture intra-treatment images of a patient volume (including the target), for registration or correlation with the diagnostic images described above in order to position the patient with respect to a treatment plan. Imaging system 835 may include any of the imaging systems described above. Treatment delivery system 830 may also include a positioning system 832 to position a patient in imaging system 835 and radiation system 831. Treatment delivery system 830 may also include a tracking system 834 capable of tracking a patient's location in imaging system 835 and in radiation system 831, as well as movement between the imaging system 835 and the radiation system 831 on the patient positioning system 832.

Treatment delivery system 830 may also include a digital processing system 833 to control radiation system 831, imaging system 835, patient positioning system 832 and tracking system 834. Digital processing system 833 may be configured to register 2D radiographic images from imaging system 835, from two or more stereoscopic projections, with digitally reconstructed radiographs (e.g., DRRs from segmented 3D imaging data) generated by digital processing system 812 in diagnostic imaging system 810 and/or DRRs generated by processing device 822 in treatment planning system 820. Digital processing system 833 may include one or more general-purpose processors (e.g., a microprocessor), special purpose processor such as a digital signal processor (DSP) or other type of device such as a controller or field programmable gate array (FPGA). Digital processing system 833 may also include other components (not shown) such as memory, storage devices, network adapters and the like. Digital processing system 833 may be coupled to radiation system 831, positioning system 832, tracking system 834 and imaging system 835 by a bus 836 or other type of control and communication interface.

Digital processing system 833 may implement methods (e.g., such as methods 900, 1000 and 1200 described above) to register images obtained from imaging system 835 with pre-operative treatment planning images in order to align the patient in the patient positioning system 832 within the treatment delivery system imaging system 835 and the radiation system 831, and to position the radiation system 831 with respect to a radiation target.

The patient positioning system 832 may include a treatment couch that may be coupled to another robotic arm (not illustrated) having five or more degrees of freedom. The robotic arm may have five rotational degrees of freedom and one substantially vertical, linear degree of freedom. Alternatively, the robotic arm may have six rotational degrees of freedom and one substantially vertical, linear degree of freedom or at least four rotational degrees of freedom. The robotic arm may be vertically mounted to a column or wall, or horizontally mounted to a pedestal, the floor or the ceiling. The treatment couch may be any type of conventional treatment table known to those of ordinary skill in the art.

Alternatively, treatment delivery system 830 may be another type of treatment delivery system, for example, a gantry-based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target region. In IMRT planning, the optimization algorithm selects subsets of the main beam and determines the amount of time that the patient should be exposed to each subset, so that the prescribed dose constraints are best met. In one particular embodiment, the gantry-based system may have a gimbaled radiation source head assembly. In one embodiment, the gantry-based system may include an electronic portal imaging device (EPID) capable of capturing images of a volume of interest using an x-ray treatment source (e.g., a LINAC) as an imaging source.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by the treatment planning system, such as the application of a beam (e.g., radiation, acoustic, etc.) and "target" may refer to a non-anatomical object or area.

Embodiments of the present invention include various operations, which are described herein. These operations may be performed by hardware components, software, firmware or a combination thereof. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of medium suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems such as in a remote diagnosis or monitoring system. In remote diagnosis or monitoring, a user may diagnose or monitor a patient despite the existence of a physical separation between the user and the patient. In addition, the treatment delivery system may be remote from the treatment planning system.

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner. Additionally, some operations may be repeated within an iteration of a particular method.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
   imaging a volume of interest (VOI) with an imaging system and acquiring positional data of a target within the VOI, wherein the positional data comprises a present position of the target relative to an imaging center of the imaging system, wherein the imaging center has a first location in a treatment room coordinate system;
   moving the VOI with a positioning system, to align the target in a radiation system that is separated from the imaging system, wherein the radiation system has a second location in the treatment room coordinate system different from the first location;
   treating the target at the second location with the radiation system;
   detecting movement of the (VOI) in the radiation system;
   returning the (VOI) from the radiation system back to the imaging system if the detected movement exceeds a movement threshold; and
   re-imaging the (VOI) with the imaging system to acquire updated positional data of the target within the (VOI).

2. The method of claim 1, wherein imaging the (VOI) in the imaging system comprises:
   acquiring 2D x-ray images of the (VOI) with the imaging system in each of two or more projections; and
   comparing the 2D x-ray images in each of the two or more projections with DRRs of the (VOI) to locate the target in the imaging system.

3. The method of claim 1, wherein acquiring the positional data comprises determining a first transformation between the present position of the target in the imaging system and the reference position of the target at the imaging center of the imaging system.

4. The method of claim 3, wherein moving the (VOI) comprises:
   moving the (VOI) from the imaging system to the radiation system over a difference vector identified by the first transformation, the difference vector comprising a difference between the imaging center and a radiation treatment center in the radiation system in the treatment room coordinate system; and aligning the target in the radiation system in conformance with a treatment plan.

5. The method of claim 4, wherein aligning the target in the radiation system comprises moving the (VOI) through the first transformation with the positioning system to align the target at the radiation treatment center.

6. The method of claim 4, wherein aligning the target comprises moving the radiation system through the inverse of the first transformation to align the radiation treatment center with the target.

7. The method of claim 3, further comprising moving the VOI through the first transformation with the positioning system to align the target at the imaging center of the imaging system with the reference position of the target at the imaging center of the imaging system.

8. The method of claim 7, wherein moving the VOI comprises moving the VOI from the imaging system to the radiation system over a difference vector comprising a difference between the imaging center and a radiation treatment center in the radiation system in the treatment room coordinate system, wherein the target is aligned at the radiation treatment center in conformance with a treatment plan.

9. The method of claim 8, wherein detecting movement of the VOI in the radiation system comprises:

determining a reference position of the VOI in the radiation system, with a tracking system, when the target is aligned at the radiation treatment center;

tracking the position of the VOI in the radiation system, during radiation treatment; and determining a second transformation between the reference position of the VOI in the radiation system and the position of the VOI during the radiation treatment.

10. The method of claim 9, further comprising realigning the target in the radiation system if a magnitude of the second transformation is less than a predetermined magnitude, wherein realigning the target comprises one of moving the VOI through the second transformation and moving the radiation system through the inverse of the second transformation.

11. The method of claim 9, further comprising halting the radiation system if the second transformation exceeds a predetermined magnitude.

12. The method of claim 11, further comprising returning the VOI to the imaging system over the inverse of the difference vector and determining the position of the target in the imaging system relative to the reference position of the target at the imaging center of the imaging system.

13. The method of claim 7, wherein detecting movement of the VOI in the radiation system comprises:

acquiring a 2D portal image of the VOI in the radiation system corresponding to a selected projection in the imaging system;

comparing the 2D portal image of the VOI with a 2D reference image of the VOI in the selected projection, wherein the 2D reference image of the VOI comprises a 2D reference x-ray image acquired by the imaging system after the target is aligned with the reference position of the target in the imaging system.

14. The method of claim 13, further comprising determining a second transformation between the 2D portal image and the 2D reference image.

15. The method of claim 14, further comprising realigning the target in the radiation system if a magnitude of the second transformation is less than a predetermined magnitude, wherein realigning the target comprises moving the VOI through the second transformation.

16. The method of claim 14, further comprising halting the radiation system if the second transformation exceeds a predetermined magnitude.

17. The method of claim 16, further comprising returning the VOI to the imaging system over the inverse of the difference vector and determining the position of the target in the imaging system relative to the reference position of the target at the imaging center of the imaging system.

18. The method of claim 1, wherein detecting movement of the VOI in the radiation system comprises:

determining a reference position of the (VOI) in the radiation system, with a tracking system, after aligning the target at the radiation treatment center;

tracking the position of the (VOI) in the radiation system, during radiation treatment, with the tracking system; and determining a second transformation between the reference position of the (VOI) in the radiation system and the position of the (VOI) during the radiation treatment.

19. The method of claim 18, further comprising realigning the target in the radiation system if a magnitude of the second transformation is less than a predetermined magnitude, wherein realigning the target comprises one of moving the VOI through the second transformation and moving the radiation system through the inverse of the second transformation.

20. The method of claim 18, further comprising halting the radiation system if the second transformation exceeds a predetermined magnitude.

21. The method of claim 20, further comprising returning the (VOI) to the imaging system over the inverse of the difference vector and determining the position of the target in the imaging system relative to the reference position of the target at the imaging center of the imaging system.

22. A system, comprising:

an imaging system configured to image a volume of interest (VOI) to acquire positional data of a target within the VOI, wherein the positional data comprises a present position of the target relative to a reference position of the target at an imaging center of the imaging system, and wherein the imaging center has a first location in a treatment room coordinate system;

a radiation system that is separated from the imaging system, the radiation system configured to apply a radiation treatment beam to the target, wherein radiation system has a second location in the treatment room coordinate system different from the first location;

a positioning system configured to move the VOI from the imaging system to the radiation system to align the target in the radiation system; and a tracking system configured to detect movement of the VOI in the radiation system;

wherein the positioning system is configured to return the VOI from the radiation system back to the imaging system if the tracking system detects movement of the VOI that exceeds a movement threshold, and wherein the imaging system is configured to re-image the VOI to acquire updated positional data of the target within the VOI in response to the return.

23. The system of claim 22, wherein the tracking system is further configured to track the VOI from the imaging system to the radiation system.

24. The system of claim 22, wherein to image the VOI the imaging system is configured to:

acquire 2D x-ray images of the VOI in each of two or more projections; and to compare the 2D x-ray images in each of the two or more projections with reference DRRs of the VOI to locate the target in the imaging system.

25. The system of claim 22, wherein to acquire the positional data, the imaging system is configured to determine a first transformation between the present position of the target in the imaging system and the reference position of the target at the imaging center of the imaging system.

26. The system of claim 25, wherein the positioning system is configured to
move the VOI from the imaging system to a radiation treatment center in the radiation system over a difference vector comprising a difference between the imaging center and the radiation treatment center in the treatment room coordinate system; and to
align the target in the radiation system in conformance with a treatment plan.

27. The system of claim 26, wherein to align the target in the radiation system, the positioning system is further configured to move the VOI through the first transformation to align the target at the radiation treatment center.

28. The system of claim 26, wherein to align the target in the radiation system, the radiation system is configured to move through the inverse of the first transformation to align the radiation treatment center with the target.

29. The system of claim 25, wherein the positioning system is configured to move the VOI through the first transformation to align the target at the imaging center of the imaging system with the reference position of the target at the imaging center of the imaging system.

30. The system of claim 29, wherein the positioning system is further configured to move the VOI from the imaging system to the radiation system over a difference vector comprising a difference between the imaging center and the radiation treatment center in the treatment room coordinate system, wherein the target is aligned at the radiation treatment center.

31. The method of claim 30, wherein to detect movement of the VOI in the radiation system, the tracking system is configured to:
determine a reference position of the VOI in the radiation system when the target is aligned at the radiation treatment center; to
track the position of the VOI in the radiation system, during radiation treatment; and to
determine a second transformation between the reference position of the VOI in the radiation system and the position of the VOI during the radiation treatment.

32. The system of claim 31, wherein the positioning system is configured to realign the target in the radiation system by moving the VOI through the second transformation if a magnitude of the second transformation is less than a predetermined magnitude.

33. The system of claim 31, wherein the radiation system is configured to halt the radiation treatment if the second transformation exceeds a predetermined magnitude.

34. The system of claim 33, wherein the positioning system is configured to return the VOI to the imaging system over the inverse of the difference vector and to determine the position of the target in the imaging system relative to the reference position of the target at the imaging center of the imaging system.

35. The system of claim 22, wherein to detect movement of the VOI in the radiation system, the tracking system is configured to
determine a reference position of the VOI in the radiation system after the target is aligned at the radiation treatment center, to
track the position of the VOI in the radiation system during radiation treatment, and to
determine a second transformation between the reference position of the VOI in the radiation system and the position of the VOI during the radiation treatment.

36. The system of claim 35, wherein the positioning system is further configured to move the VOI through the second transformation to realign the target with the radiation treatment center if a magnitude of the second transformation is less than a specified magnitude.

37. The system of claim 35, wherein the radiation system is configured to move through the inverse of the second transformation realign the radiation treatment center with the target if a magnitude of the second transformation is less than a specified magnitude.

38. The system of claim 35, wherein the radiation system is configured to halt radiation treatment if the second transformation exceeds the predetermined magnitude.

39. The system of claim 38, wherein the positioning system is configured to return the VOI to the imaging system over the inverse of the difference vector and wherein the imaging system is configured to determine the position the target in the imaging system relative to the reference position of the target at the imaging center of the imaging system.

40. A system, comprising:
an imaging system configured to image a volume of interest (VOI) to acquire positional data of a target within the VOI, wherein the positional data comprises a present position of the target relative to a reference position of the target at an imaging center of the imaging system, wherein to acquire the positional data, the imaging system is configured to determine a first transformation between the present position of the target in the imaging system and the reference position of the target at the imaging center of the imaging system, the imaging center having a first location in a treatment room coordinate system;
a radiation system including a portal imaging device, wherein the radiation system is configured to apply a radiation treatment beam to the target and to capture electronic portal images of the VOI; and
a positioning system configured to apply the first transformation to the VOI to align the target with the reference position of the target at the imaging center of the imaging system and to move the VOI from the imaging system to the radiation system to align the target in the radiation system, wherein the radiation system has a second location in the treatment room coordinate system different from the first location.

41. The system of claim 40, wherein the portal imaging device is configured to detect movement of the VOI in the radiation system.

42. The system of claim 41, wherein to detect movement of the VOI in the radiation system, the portal imaging device is configured to:
acquire a 2D portal image of the VOI in the radiation system corresponding to a selected projection of the VOI in the imaging system; and to
compare the 2D portal image of the VOI with the 2D reference image of the VOI in the selected projection, wherein the 2D reference image of the VOI comprises a 2D reference x-ray image acquired by the imaging system after the target is aligned with the reference position of the target at the imaging center.

43. The system of claim 42, wherein the radiation system is further configured to determine a second transformation between the 2D portal image and the 2D reference image.

44. The system of claim 43, wherein the positioning system is configured realign the target in the radiation system by moving the VOI through the second transformation if a magnitude of the second transformation is less than a specified magnitude.

45. The system of claim 43, wherein the radiation system is configured to halt the radiation treatment if a magnitude of the second transformation exceeds a specified magnitude.

46. The system of claim 45, wherein the positioning system is configured to return the VOI to the imaging system over the inverse of the difference vector and wherein the imaging system is configured to determine the position the target in the imaging system relative to the reference position of the target at the imaging center of the imaging system.

47. The system of claim 40, wherein to image the VOI the imaging system is configured to:
acquire 2D x-ray images of the VOI in each of two or more projections; and to
compare the 2D x-ray images in each of the two or more projections with reference DRRs of the VOI to locate the target in the imaging system.

48. The system of claim 40, wherein the positioning system is configured to move the VOI from the imaging system to the radiation system over a difference vector comprising a difference between the imaging center and a radiation treatment center in the radiation system in the treatment room coordinate system to align the target at the radiation treatment center in the radiation system.

49. An apparatus, comprising:
means for imaging a radiation target at a first location in an imaging system;
means for treating the radiation target in a radiation system that is separated from the imaging system at a second location that is different from the first location, wherein the second location is different from the first location to prevent interference between the imaging and the treating;
means for moving the radiation target from the first location to the second location after the imaging;
means for detecting movement of the radiation target during the treating; and
means for returning the radiation target back to the first location if the movement of the radiation target exceeds a movement threshold.

50. The apparatus of claim 49, further comprising means for compensating for the movement of the radiation target if the movement of the radiation target does not exceed the movement threshold.

51. The apparatus of claim 49, further comprising means for correcting the movement of the radiation target if the movement of the radiation target does not exceed the movement threshold.

52. The apparatus of claim 49, wherein the first location is an imaging center of the imaging system.

* * * * *